US006323390B1

(12) United States Patent
Wu et al.

(10) Patent No.: US 6,323,390 B1
(45) Date of Patent: Nov. 27, 2001

(54) TRANSGENIC MOUSE MODELS FOR HUMAN BLADDER CANCER

(75) Inventors: Xue-Ru Wu, Woodside; Tung-Tien Sun, Scarsdale, both of NY (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 09/083,541

(22) Filed: May 22, 1998

Related U.S. Application Data

(63) Continuation-in-part of application No. 08/969,315, filed on Nov. 13, 1997, which is a continuation-in-part of application No. 08/907,800, filed on Aug. 8, 1997, now Pat. No. 6,001,646, which is a continuation-in-part of application No. 08/464,961, filed on Jun. 5, 1995, now Pat. No. 5,824,543.

(51) Int. Cl.$^7$ ............................ C12N 15/09; C12N 15/63; C12N 15/00; C12N 5/00
(52) U.S. Cl. ............................ 800/18; 800/13; 800/14; 800/21; 800/22; 800/25; 800/10; 435/455; 435/320.1; 435/325
(58) Field of Search .................. 800/13, 18, 21, 800/22, 25, 10, 14; 435/455, 320.1, 325

(56) References Cited

PUBLICATIONS

Hammer et al., Journal of Animal Science, vol. 63, pp. 269–278, 1986.*

Ebert et al., Molecular Endocrinology, vol. 2, pp. 277–283, 1988.*

Mullins et al., Journal of Clinical Investigations, vol. 998, No. 11, pp. S37–S40, 1996.*

Wall, Theriogenology, vol. 45, pp. 57–68, 1996.*

Kappel et al., Current Opinion in Biotechnology, vol. 3, pp. 548–553, 1992.*

Strojek & Wagner, Genetic Engineering: Principles and Methods, vol. 10, pp. 221–246, 1988.*

Database Medline on Dialog, US National Library of Medicine, No. 97137677 (1996).

Database Medline on Dialog, US National Library of Medicine, No. 95148601 (1995).

Database Medline on Dialog, US National Library of Medicine, No. 96373865 (1996).

Database Medline on Dialog, US National Library of Medicine, No. 92297161 (1992).

* cited by examiner

*Primary Examiner*—Jill D. Martin
(74) *Attorney, Agent, or Firm*—Browdy & Neimark

(57) ABSTRACT

A transgenic mouse, containing an oncogene or a tumor suppressor gene operably linked to a urothelium-specific promoter in its germ cells and somatic cells serves as an animal model system for human bladder cancer.

9 Claims, 16 Drawing Sheets

```
 811 TTCACTCCTATTCCCCTCAGTGGTTAAGTCAGACTTTGTGGTGCCTCCATGTCGGGGCGCAGGGAGCTTGTGAGCGTGGTGGACAGTG
          V  K  S  D  F  V  V  P  P  C  R  G  R  R  E  L  V  S  V  V  D  S  G
         2⎦                                                                   *
 901 GGTCTGGCTACACCGTCAGCGCTCACAAGGCTCACGCCATATCAGTGACAAACTAACACCAGGAACCAAATACTAGTACCGATGGACACCT
      S  G  Y  T  V  T  R  L  S  A  Y  Q  V  T  N  L  T  P  G  T  K  Y  Y
 991 GTGGAGGTGGGATGGCAAAAAGGGAAGTGGAGGTCCCGTGAGGGTGGGAAGCATGAGTTAGAGAGGCACAGCTAAAG           3
1081 GGTAGGAGAATGTGAACCTGACCCCAGAGGGGACACATAGCTAGAAGTGGAGGCTGGAACCCCTCCGAGTGCCAG
1171 ATACGTACAACCCTGCTTTCTCCAACTCCGCCTTCTAAAGCATATCCTACCGAGTCGAGTACAGAGAAGGGACGTCGAGTCCAGAG
         3⎦ I  S  Y  R  V  Q  K  G  T  S  T  E  S  S  P  E
1261 ACTCCCATGTCCACGCTTCCTCGTTAAGTAAAATGCCCGTCTCTCACACTTCCCTAAGCTCCGACTTTTTCTCCTAGAGCAAGTTAGCT
      T  P  M  S  T  L  P  R
1351 AAACTGTTTCCCGAGTGCTCAGTGCCACACACACCCCCCCAACCCCCTCCTGTCCTCCTGTGTATGGCCCCTCCTGTCCTGTTCAATCATCT
        4⎦
1441 CTGCACTAGAGGTTCCTTGTGCAGAGCGGATGATGTCCCTAAGTGTTGCTGTGAGGGGGTCTATGTTTGCTTGACTG
1531 GTTGGCTGATGACCAGTGATGAACTGATGTCTGGAGGCTGGGCTAATGGCTAGAGGCTGTGAACCACAGGAGCTACCTAGGAACCCTT
1621 CAACTCACAGAGAGTTCCCCCATTCTTCTCTGACAGAGAAAAAACATGGAGTCTATTGGGTTAGGAATGGCCCGGACAGGAGGATGGTGGT
         4⎦ K  N  M  E  S  I  G  L  G  M  A  R  T  G  G  M  V  V
1711 CATCACAGTGCTGCTGTCTGTGGCCATGTTCCTGTTGGTCGTGGGTCTTATTGTTGCCCTGCACTGGGATGCCCGCAAATGAAAAGGGCT
      I  T  V  L  S  V  A  M  F  L  L  V  G  L  I  V  A  L  H  W  D  A  R  K  *
1801 CTCCTGCATCCAGGCTCCTCCAAGAAGTCCAGCCTGTAGTCACCTTGCCAGGCTGTAGTCACTGGCTTCTCAGTGGCTTTCTTCCCTCTCCC
1891 CGCCCCCTCCTCCGAGTCCGAGTTCCTGACAGTGCCCCCCCTCCCTGTCTCCACCTTGCAGCACTCCCTGCTAGCCACACAGGTCAATCCT
1981 GCCAACACTGATTATCTCTTAACTGTACTTAAGCTGACCCACGTAGTATGTCTCATCTCCGACCATGTCTATGTG
2071 AGTCACCCCTTAGCTGGTCCCCTTATGCACATATCAAAACTACCAAGTCACGTCATGTCATTTCTCTATCCCAAACCCA
2161 AGGGTGACTTTTACCAGAGGAGCAAGTCAGAGAGATAATGAAGCCTCAGTTGGCAGGGGGTAGAAGCTGGATCACCATGTGAGCCT
2251 AGGGCTTGGGTTTTGCATCCTGACAGAACTAGGAAGAAGACACAAACAGGCAGCCCCTCCAGCCTGGGTGAAGAACATGCTAAACGGT
2341 GACTGGGAAGCTGACAGAGCCGAGTGGACGGAAGCTCCTGGAAGGGGGACACACATAGGTAAACAGCAGTGCACCCTCGTCC
2431 TCTAGACCCCTGAGCCCTAGAATATAGTTTGTTCTATAAAAGTTTCTATTATTTTATTTTGTTTGTTTTTCCAGAGCTGAGG
2521 ATTTTTAAAATATAGTTTGTTCTATAAAAGTTTCTATTATTTTATTTTGTTTGTTTTTCCAGAGCTGAGG
2611 CAAAAACCCAGACTTGAGCTTGCTAGGCAAGTGCTCTACCACTGAGCTAAATCCCCAACCCCTGTTTTGTTTTTTTGAAGCAGGGTT
2701 TCTCTGTGTAGCCTCTGGCTGTCCTAGAGCTC   2731
```

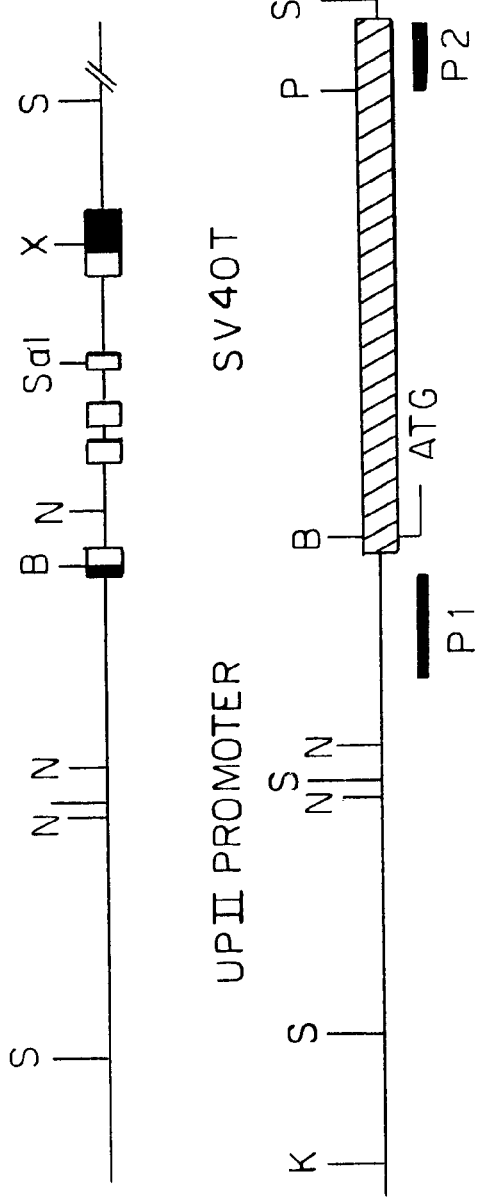

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 3963 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GAGCTCAGGT CCTATCGAGT TCACCTAGCT GAGACACCCA CGCCCCTGCA GCCACTTTGC      60

AGTGACAAGC TGAGTCTCA GGTTCTGCAT CTATAAAAAC GAGTAGCCTT TCAGGAGGGC      120

ATGCAGAGCC CCCTGGCCAG CGTCTAGAGG AGAGGTGACT GAGTGGGGCC ATGTCACTCG      180

TCCATGGCTG GAGAACCTCC ATCAGTCTCC CAGTTAGCCT GGGGCAGGAG AGAACCAGAG      240

GAGCTGTGGC TGCTGATTGG ATGATTTACG TACCCAATCT GTTGTCCCAG GCATCGAACC      300

CCAGAGCGAC CTGCACACAT GCCACCGCTG CCCCGCCCTC CACCTCCTCT GCTCCTGGTT      360

ACAGGATTGT TTTGTCTTGA AGGGTTTTGT TGTTGCTACT TTTTGCTTTG TTTTTTCTTT      420

TTTAACATAA GGTTTCTCTG TGTAGCCCTA GCTGTCCTGG AACTCACTCT GTAGACCAGG      480

CTGGCCTCAA ACTCAGAAAT CCACCTTCCT CCCAAGTGCT GGGATTAAAG GCATTCGCAC      540

CATCGCCCAG CCCCCGGTCT TGTTTCCTAA GGTTTTCCTG CTTTACTCGC TACCCGTTGC      600

ACAACCGCTT GCTGTCCAAG TCTGTTTGTA TCTACTCCAC CGCCCACTAG CCTTGCTGGA      660

CTGGACCTAC GTTTACCTGG AAGCCTTCAC TAACTTCCCT TGTCTCCACC TTCTGGAGAA      720

ATCTGAAGGC TCACACTGAT ACCCTCCGCT TCTCCCAGAG TCGCAGTTTC TTAGGCCTCA      780

GTTAAATACC AGAATTGGAT CTCAGGCTCT GCTATCCCCA CCCTACCTAA CCAACCCCCT      840

CCTCTCCCAT CCTTACTAGC CAAAGCCCTT TCAACCCTTG GGGCTTTTCC TACACCTACA      900

CACCAGGGCA ATTTTAGAAC TCATGGCTCT CCTAGAAAAC GCCTACCTCC TTGGAGACTG      960

ACCCTCTACA GTCCAGGAGG CAGACACTCA GACAGAGGAA CTCTGTCCTT CAGTCGCGGG      1020

AGTTCCAGAA AGAGCCATAC TCCCCTGCAG AGCTAACTAA GCTGCCAGGA CCCAGCCAGA      1080

GCATCCCCCT TTAGCCGAGG GCCAGCTCCC CAGAATGAAA AACCTGTCTG GGGCCCCTCC      1140

CTGAGGCTAC AGTCGCCAAG GGGCAAGTTG GACTGGATTC CCAGCAGCCC CTCCCACTCC      1200

GAGACAAAAT CAGCTACCCT GGGGCAGGCC TCATTGGCCC CAGGAAACCC CAGCCTGTCA      1260

GCACCTGTTC CAGGATCCAG TCCCAGCGCA GTATGGCATC CACACTGCCT GTCCAGACCT      1320

TGCCCCTGAT CCTGATTCTG CTGGCTGTCC TGGCTCCGGG GACTGCAGGT CTCTATTGCT      1380

GGTGGGTGCG AGGAGGGTTT CAGAGCGCTA GACAGGGAAC ATTGTCTCCC CAGGGCTCTC      1440

AAGGACAGGA ATGTTGGTCT AGCTGGTTGG GGTTGAGAGT TACTAGTGGT AGGAATCAGG      1500

TGACAAATTC CTGGGCTTCT TCCCAGATCC AGGAGTCAAG AAATTTGGGT AAGTGTCCAA      1560

GGTTTGTGTG AGTTGGGCGA GACTGGGGAC TGACTGGGTG CCATGGTCTA GTTTGGGTCG      1620

GTAGGGCTAT CTGGCTCCCA ACAGCGCGGC GTACCCACCA TCTGCAGATC AAGCCTGCCA      1680

TCTGGTGGTC AGATCCACAC GCTCCTCTTC TGTCTCTGCA CCCTTAGCAA TGACCACCCA      1740

CCCACCCCGC CAGCTCTGAG TTAAGAGGGG GCTAACTCCT GAGTTCCCTC TCGGCTCCCT      1800
```

-continued

```
AACAGACTTC AACATCTCAA GCCTCTCTGG TCTGCTGTCT CCGGCGCTAA CAGAAAGCCT      1860

GTTAATTGCC TTGCCCCCAT GTCACCTCAC GGGAGGTAAT GCCACATTGA TGGTCCGGAG      1920

AGCCAACGAC AGCAAAGGTA GACCTCCCTT GTACCCATTT ATTCTACTCG TCGTAACCCC      1980

TCTTAACGAT ACCCAAGAGC TGCCCGTTCT ACAAGAGTGG ACGCTAGAAT CTGATCTTGC      2040

CTTTCACTCC TATTTCCCCT CAGTGGTTAA GTCAGACTTT GTGGTGCCTC CATGTCGCGG      2100

GCGCAGGGAG CTTGTGAGCG TGGTGGACAG TGGGTCTGGC TACACCGTCA CAAGGCTCAG      2160

CGCATATCAG GTGACAAACC TAACACCAGG AACCAAATAC TAGTAGGTAC CGATGGACAC      2220

CTGTGGAGGT GGGATGGCAA AAAGGGAAG TGGAGGTCCC GTGAGGGTGG GGAAGTGCCG       2280

GGAAGCATGA GTTAGAGAGG GCACAGCTAA AGGGTAGGAA ATGTGAACCT GGACCCCAGG     2340

AGGGCCCAGA TGGACACAT AGCTAGAAGG TGGAGGCTGG AACCCCTCCT CCCGAGTGCC      2400

AGATACGTAC AACCTCTGCT TTCTCTCAAC TCCGCCTCTA AAGCATATCC TACCGAGTAC     2460

AGAAGGGGAC GTCGACCGAG TCCAGTCCAG AGACTCCCAT GTCCACGCTT CCTCGTTAAG     2520

TAAAATGCCC GTCTCTCACA CTTCCCTAAG CTCCGACTTT TTTCTCCTAG AGCAAGTTAG     2580

CTAAACTGTT TCCCGAGTGC TCAGTCGCAC ACACACCCCC TCCCCAACCC CCAGTATTT      2640

GGTATGGCCC CTCCTGTCCT GTTCAATCAT CTCTGCACTA GAGGTTCCTT GTGCAGAGGG     2700

ATGATGTCCT CCTTGGTGGC TCCTAAGTGT TGCTGTGAGG GGGGTCTATG TTTGCTTGAC     2760

TGGTTGGCTG GATGACCAGT TGAACTGATG CTGGAGGCTA CTGGATGGCT GGGCTAATGC     2820

TGTGAACCAC AGGAGCTACC TAGGAACCCC TTCAACTCAC AGAGGTTCCC CCATCTTCTT     2880

CTGACAGGAA AAAACATGGA GTCTATTGGG TTAGGAATGG CCCGGACAGG AGGGATGGTG     2940

GTCATCACAG TGCTGCTGTC TGTGGCCATG TTCCTGTTGG TCGTGGGTCT TATTGTTGCC     3000

CTGCACTGGG ATGCCCGCAA ATGAAAAGGG CTCTCCTGCA TCCCAGGCTC CTCCAAGAAG     3060

TCCAGCCTGC CTCCTGCCAG GCTGTAGTCA CTGGCTTCTC AGTGGCTTTT CTTCCCTCTC     3120

CCCGCCCCCT CCTCGAGTCC ACTCCTGACA GTGCCCCCTC CCTGCTCCCT GTCTCACCTT     3180

GCAGCACTCC CTGCTAGCCC CACTGCAATC CTGCCAACAC TGATTTATCT CTTAACTGTA     3240

CTTAATTCTC ACAATAAAGG CTGACCCACG TAGTATGTCT CATCTCCGAC CATGTCTATG     3300

TGAGTCACCC CTTTAGCTGG TCCCCTTATG CACATATCAA AACTACCAAT GTCAAGGTCA     3360

CGTGCATGTC ATTTTCTCTA TCCCAAACCC CAAGGGTGAC TTTTACCAGG AGGGAGGCAA     3420

GCAGAGGCAG AGATAATGAA GCCTCAAGCC CAGACTAGGG AAGCCCTCCA AGCCCCAGAC     3480

CTAGGGCTTG GGTTTTGCAT CCTGCACTCA GTAGATACCC AAGCAGGAGT CTAGTTGGGC     3540

AGGGGGTAGA AGCTGGATCA CCATGTGAGC CTGACTGGGA AGCTGACAGA ACTAGGGAAG     3600

AACTAGAGAA AACACAAACA GGGCAGGCCC TCCAGCCCTG GGTGAAGAAC ATGCTAAACG     3660

GTTCTAGACC CCTAGAGCCG AGGTGGACGG AAGCTCCTGG AAGGGGGAGG GGGGACACA     3720

ACATAGGTAA ACAGGCAGTG GCACCCTCGT CCATTTTTAA AATATAGTTT TGTTCTATAA    3780

AAGTTTTATT TATTTATTTA TTTGCTTGTT TTTATTTGTT TGTTTGTTTT CCAGAGCTGA    3840

GGCAAAAACC CAGGACCTTG AGCTTGCTAG GCAAGTGCTC TACCACTGAG CTAAATCCCC    3900

AACCCCTGTT TTTGTTTTTT TGAAGCAGGG TTTCTCTGTG TAGCTCTGGC TGTCCTAGAG    3960

CTC                                                                   3963
```

(2) INFORMATION FOR SEQ ID NO:2:

(i) SEQUENCE CHARACTERISTICS:

```
            (A) LENGTH: 26 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Met Ala Ser Thr Leu Pro Val Gln Thr Leu Pro Leu Ile Leu Ile Leu
1               5                  10                  15

Leu Ala Val Leu Ala Pro Gly Thr Ala Asp
            20                  25

(2) INFORMATION FOR SEQ ID NO:3:

(i) SEQUENCE CHARACTERISTICS:
            (A) LENGTH: 44 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Phe Asn Ile Ser Ser Leu Ser Gly Leu Leu Ser Pro Ala Leu Thr Glu
1               5                  10                  15

Ser Leu Leu Ile Ala Leu Pro Pro Cys His Leu Thr Gly Gly Asn Ala
            20                  25                  30

Thr Leu Met Val Arg Arg Ala Asn Asp Ser Lys Val
            35                  40

(2) INFORMATION FOR SEQ ID NO:4:

(i) SEQUENCE CHARACTERISTICS:
            (A) LENGTH: 46 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Val Lys Ser Asp Phe Val Val Pro Pro Cys Arg Gly Arg Arg Glu Leu
1               5                  10                  15

Val Ser Val Val Asp Ser Gly Ser Gly Tyr Thr Val Thr Arg Leu Ser
            20                  25                  30

Ala Tyr Gln Val Thr Asn Leu Thr Pro Gly Thr Lys Tyr Tyr
            35                  40                  45

(2) INFORMATION FOR SEQ ID NO:5:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Ile Ser Tyr Arg Val Gln Lys Gly Thr Ser Thr Glu Ser Ser Pro Glu
1               5                  10                  15

Thr Pro Met Ser Thr Leu Pro Arg
            20
```

(2) INFORMATION FOR SEQ ID NO:6:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Lys Asn Met Glu Ser Ile Gly Leu Gly Met Ala Arg Thr Gly Gly Met
1               5                   10                  15

Val Val Ile Thr Val Leu Leu Ser Val Ala Met Phe Leu Leu Val Val
            20                  25                  30

Gly Leu Ile Val Ala Leu His Trp Asp Ala Arg Lys
        35                  40
```

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GGATCCTCAG TCTGAGTCAG GCCCCA                                                      26

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GGATCCACTG GATGACTGCC ATGGAGG                                                    27

TRANSGENIC MOUSE MODELS FOR HUMAN BLADDER CANCER

CROSS-REFERENCE TO RELATED APPLICATIONS

The present application is a continuation-in-part of application Ser. No. 08/969,315, filed Nov. 13, 1997, which is a continuation-in-part of application Ser. No. 08/907,800, filed Aug. 8, 1997, now U.S. Pat. No. 6,001,646, which is a continuation-in-part of application Ser. No. 08/464,961, filed Jun. 5, 1995, now U.S. Pat. No. 5,824,543, the entire contents of all three prior applications are hereby incorporated by reference.

GOVERNMENT LICENSE RIGHTS

The U.S. Government has a paid up license in this invention and the right in limited circumstances to require the patent owner to license others on reasonable terms as provided for by the terms of National Institutes of Health Grant Nos. DK39753 and DK49469 and a Veterans Administration Merit Review Grant.

BACKGROUND OF THE INVENTION

1. Field of the Invention

The present invention relates to transgenic animal models for human bladder cancer and their use as in vivo models for testing potential carcinogens, preventative measures, as well as therapeutic modalities for intervention in the progression of human bladder cancer.

2. Description of the Related Art

Bladder cancer is the fifth most common cancer affecting predominantly the aging male population and the twelfth leading cause of cancer deaths. Despite aggressive therapy, bladder cancer still continues to be one of the leading causes of cancer deaths in the United States. The American Cancer Society estimated that in 1997 there were 54,500 new cases diagnosed and 11,700 deaths resulting from this disease in the United States.

A major cornerstone in bladder cancer research is the recognition of two distinct forms of bladder cancer (Koss, 1985 and 1992). About 80% of transitional cell carcinomas (TCCs) are superficial, well-differentiated, papillary tumors. This type of TCC is often multifocal and recurrent but rarely progresses to muscle invasion. Another type accounts for 20% of all TCCs and is either present as a carcinoma in situ (CIS) or as poorly differentiated, invasive tumors. It is believed that the majority of invasive TCCs are not derived from the superficial type but directly from CIS and related urothelial abnormalities (Koss, 1992). Interestingly, recent genetic studies suggest that these two forms of bladder cancer may have distinct underlying genetic causes. Cordon-Cardo et al. (1994) proposed that the inactivation of p16 may be responsible for the formation of superficial TCCs, while the inactivation of p53 underlies the invasive form of TCCs.

A set of growth-promoting and growth-inhibiting genes tightly controls cellular growth and differentiation and serves to ensure normal development and to safeguard tissue homeostasis. Alterations in the genes can lead to cellular transformation and tumor formation (Witkowski, 1990; Hunter 1997). Research in the past two decades has identified two classes of genes whose alterations play a major role in tumorigenesis. The first class of genes is oncogenes that were initially identified in studies on retroviruses (Bishop, 1991). These genes have cellular counterparts, proto-oncogenes, that promote normal cell growth; but when activated by a point mutation or induced to overexpress, these genes can promote tumorigenesis in a dominant fashion. The second class of genes is tumor suppressor genes that suppress cell growth, and their mutation or functional inactivation can also contribute to tumorigenesis (Weinberg, 1991). Unlike oncogenes, tumor suppressor genes act in a recessive manner, because the loss of activity requires the inactivation of both alleles. Studies from a variety of human solid tumors suggest that the concerted activity of these two classes of genes underlie tumor development and progression (Finlay, 1993; Vogelstein et al, 1993; Hoskins et al, 1994).

Many genetic alterations involving both oncogenes and tumor suppressor genes have been associated with bladder cancer. Of these, the most notable are the activating mutation of Ha-ras oncogene, the overexpression of neu/erbB-2 and myc oncogenes, and the inactivating mutations of tumor suppressor genes, p53, p16 and retino blastoma gene (Rb) (Borland et al, 1992; Knowles, 1995; Cordon-Cardo et al, 1997) discussed below.

Ha-ras (H-ras): Activating mutations of the ras gene family (Ha-, K- and N-ras) are detected in about 30% of all human tumors, making them the most frequently mutated oncogenes (Bos, 1989; Fearon et al, 1990). Ras mutations found in human tumor and experimental animal models involve predominantly codons 12, 13 and 61. Although ras mutation was first identified in bladder cancer (Capon et al, 1983), its precise role in bladder cancer formation remains unsettled. First, differences in ras mutation frequency has been noted. Earlier functional assays detected ras mutations in 7–16% of bladder cancers (Fujita et al, 1985; Pulciani et al, 1987). More recent data from Koss and colleagues using more sensitive assays detected a much higher rate of up to 40% (Czerniak et al, 1992). Second, it remains unclear whether ras activation can act as an initiating event in bladder cancer formation. Ras mutations are believed to be an initiating event in skin, lung, breast and bowel tumors (Daya-Grosjean et al, 1993; Finlay, 1993; Vogelstein, 1993; Li et al, 1994; Hoskins et al, 1994). In bladder cancer, however, ras mutations have been primarily associated with higher grade, later stage tumors (Levesque et al, 1993). Third, the transformation potential of ras oncogene remains controversial. While activated ras alone can efficiently transform immortal cell lines, it requires the cooperative activity of another oncogene (myc) or a dominant-negative p53 to transform primary rodent cells (Coopersmith et al, 1997; Serrano et al, 1997). On the other hand, the high-level expression of activated ras can circumvent the need for a cooperating oncogene to transform rodent cells (Mann et al, 1991).

Neu/erbB-2: The erb-B2 proto-oncogene encodes a receptor tyrosine kinase with sequence homology to epidermal growth factor (EGF) receptor (Hynes et al, 1994). Amplification of erbB-2 gene was found in 14% of human TCCs overall, but in up to 46% of grade 3 tumors (Coombs et al, 1991). Increased expression of erbB-2 protein (p185) can be detected in an even higher percentage (30–60%) of late stage TCCs, suggesting a correlation between erb-B2 overexpression and tumor progression (Asamoto et al, 1990; Zhau et al, 1990). It has been suggested that amplification/overexpression of erbB-2 enhances cellular mitogenic signaling, thus accelerating tumorigenesis (Hynes et al, 1994). Despite the demonstrated correlation between erbB-2 overexpression and late-stage TCC, little is known about the tumor-initiating and -promoting potential of this gene in bladder epithelium.

c-myc: The c-myc proto-oncogene encodes a transcription factor that regulates cell proliferation and differentiation.

Altered expression of c-myc gene is a common event in a variety of tumors including bladder cancer. Overexpression of c-myc protein, but not gene amplification, has been found in a significant number (up to 59%) of TCCs (Schmitz-Drager et al, 1997). However, the correlation of the c-myc overexpression with tumor stage is somewhat controversial, as different reports have shown either correlation with early (Masters et al, 1988; Sauter et al, 1995) or late (Kotake, 1990) stages or no correlation (Grimm et al, 1995; Kubota et al, 1995; Lipponen, 1995; Schmitz-Drager et al, 1997).

p53: A nuclear phosphoprotein, p53, plays a key role in cell cycle control, particularly in G1-S phase transition. Inactivating mutations of p53 can result in genome instability which predisposes cells to malignancy (Levine, 1997; Paulovich et al, 1997). The p53 gene can be inactivated by mutation or deletion of both alleles. It can also be functionally inactivated by a dominant-negative p53 mutant, which forms inactive hetero-oligomers with wild-type p53. In addition, it can be inactivated by oncogene products of DNA tumor viruses including SV40 large T antigen, adenoviral EIB protein, and papilloma viral protein EG (Vogelstein et al, 1992). p53 mutation is the most frequent genetic alteration in bladder cancer (50–60%). A number of studies have shown that p53 mutations occur in relatively late stages of human bladder cancer, suggesting that loss of p53 function is related to tumor invasion and progression (Reznikoff et al, 1996; Cordon-Cardo et al, 1997).

Rb: The functional inactivation of retinoblastoma gene (Rb) involving both alleles is found in around 30% of bladder cancer patients (Benedict, 1992). There is also a strong correlation between Rb inactivation and tumor stage. Cordon-Cardo and colleagues (1992) showed that Rb expression is altered in 38 of 48 muscle invasive bladder tumors, but only in 10 of 48 superficial tumors, suggesting that loss of Rb function contributes to bladder tumor progression.

p16: It has been suggested that chromosomal region 9p21 harbors a tumor suppressor gene because the loss of this region is identified in a significant number of bladder tumors. The search for this suppressor gene has led to the identification of the p16 gene. It is now known that p16 encodes a protein that inhibits the activity of cyclin-dependent kinase 4 and that is mutated in a wide variety of cancers (Kamb et al, 1994). p16-deficient mice are viable but highly prone to spontaneous and carcinogen-induced tumors (Serrano et al, 1996). In bladder cancer, the p16 mutation has been found in about 18% of the cases and is predominantly associated with low grade bladder tumors (Gruis et al, 1995; Orlow et al, 1995).

Although the genetic alterations involving the activation of oncogenes and inactivation of tumor suppressor genes are prevalent in human bladder cancer, their exact role in the multi-step bladder tumorigenesis has not been clearly defined. It remains unknown whether any of these alterations are responsible for the cellular transformation in normal urothelium and tumor progression, or some of them merely represent secondary events of well-advanced tumors (Adams et al, 1991; Fowlis et al, 1993).

SV40 large T antigen (SV40 Tag): As discussed above, p53 and Rb tumor suppressor genes frequently have loss-of-function mutations in human bladder cancer. SV40 Tag is an oncogene from DNA tumor virus, Simian Virus 40, SV40 that has been extensively used to study the role of p53 and Rd dysfunction in tumorigenesis. When introduced into host cells, SV40 Tag acts as a potent growth stimulator by inactivating p53 and Rb proteins, leading to uncontrolled cellular proliferation and tumor formation (Bryan et al, 1994).

Advances in recombinant DNA and genetic technologies have made it possible to introduce and express a desired recombinant gene sequence in a recipient animal. When only some of the animal's cells contain and express the introduced gene sequence while other cells do not, i.e., remain unaltered, the animal is known as a "chimeric" animal. The capacity of a chimeric animal to transmit the introduced gene sequence is present in the germ cells of the animal. Accordingly, only certain chimeric animals can pass along the desired gene sequence to their progeny.

By contrast, a "transgenic" animal contains the introduced gene sequence ("transgene") in all cells, and therefore, every transgenic animal is capable of transmitting the transgene to its progeny. The study of the molecular mechanism of tumorigenesis has been greatly facilitated in recent years by the use of a transgenic approach. This approach has made it possible to transfer genes of interest into a living animal which expresses the transgenes in desired tissues (Babinet et al, 1989). Transgenic animals containing and expressing oncogenes or tumor suppressor genes have been observed to be tumor-susceptible and/or to develop tumors (U.S. Pat. Nos. 4,736,866; 5,491,283; 5,550,316; 5,569,824; Stewart et al, 1984; Adams et al, 1985; Hanahan, 1985; Lacey et al, 1986; Palmiter et al, 1986; Cory et al, 1988). The specific effects or well-defined oncogenes or mutated tumor suppressor genes on cellular growth and differentiation can be assessed and correlated with multistage tumorigenesis under in vivo physiological conditions (Hanahan, 1989; Landel et al, 1990). The transgenic approach has also made it possible to study the cooperative activity of different oncogenes and mutated tumor suppressor genes by generating bi-transgenic animals that harbor two distinct genetic alterations (Berns, 1991; Fowlis et al, 1993). However, despite the clinical importance of bladder cancer, few animal models are available to study the molecular pathogenesis of bladder tumorigenesis. Although bladder tumors have been previously produced in rat urinary bladders using various chemical carcinogens, those tumors bear little similarity with those occurring in humans. Therefore, the value of these rat bladder tumors as a model system for human bladder cancers is limited.

Previous knowledge about the genetic alterations in bladder cancer formation largely derived from studies of well-advanced human bladder cancers. However, it is difficult to determine whether these alterations are the cause or the consequence of cancer development. Chemical carcinogenesis is capable of inducing bladder cancer formation, but the resulting genetic changes are often complex, and the resulting bladder phenotypes have little in common with the human counterpart.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to overcome the above-mentioned difficulties in the prior art by providing a bladder cancer model in a non-human animal where a specific genetic change can be correlated with a particular phenotype. In particular, transgenic mouse models of bladder cancer were generated where oncogenes and mutated tumor suppressor genes are expressed in the mouse epithelium under the control of a urothelial tissue specific promoter.

As specific embodiments, transgenic mice all of whose germ cells and somatic cells contain a recombinant construct or "transgene" in which an oncogene, such as SV40 Tag and H-ras, or a tumor suppressor gene, such as p53, is operably linked to the urothelium-specific uroplakin II promoter, were developed by introducing the transgene into mice or ancestors thereof of an embryonic stage.

The present invention further provides for a transgenic non-human animal model in which a combination of genes, such as a combination of an oncogene and a tumor suppressor gene, each of which is operably linked to a urothelium-specific promoter, is present in all germ cells and all somatic cells of the non-human animal.

BRIEF DESCRIPTION OF THE DRAWINGS

FIGS. 1A and 1B show the organization and nucleotide sequence of the mouse uroplakin II (UPII) genomic DNA. FIG. 1A provides the exon-intron organization of mouse UPII gene. The open and filled thick boxes denote the five coding sequences (exons) and non-coding sequences, respectively, of the gene. The open and filled thin boxes represent a $(CA)_n$ dinucleotide repeat region and an Alu-like murine B1 repeat, respectively. G1 and G2 designate two independent and partially overlapping genomic clones. The restriction sites are SacI (S), -NcoI (N), BamHI (B), SalI (Sal), and XhoI (X). FIG. 1B provides the nucleotide sequence (SEQ ID NO:1) of a 4-kb SacI fragment of mouse UPII gene. A reversed B1 repetitive sequence (in the 5' upstream region) and a potential polyadenylation site (AATAAA; in the 3' untranslated region) are underlined and double-underlined, respectively. The wavy arrow denotes the transcriptional initiation site. Broken arrows marked 1 to 4 denote the intron/exon junctions of the four introns. The predicted first amino acid residue of mature UPII protein sequence is marked with an asterisk. The preceding domain contains a pre and a pro sequence of 25 and 59 amino acids, respectively. The five exons encode SEQ ID NOs:2–6.

FIG. 3A provides a restriction map (abbreviations as described in FIG. 1A) of the endogenous murine UPII gene. A 500-bp PCR fragment (thick bar) was used as a probe which detects a 1.4-kb NcoI fragment of the endogenous UPII genome but a shorter 1.1-kb NcoI fragment of the transgene. FIG. 3B provides a restriction map of the transgene. A 3.6-kb 5'-flanking sequence of the UPII gene was inserted into an *Escherichia coli* β-galactosidase (β-gal)-encoding placF vector. In this particular test expression vector, a sequence containing a part of exon 1 and all of intron 1 and exon 2 of the mouse protamine-1 gene (mp1) was placed at the 3'-end of the β-gal (or LacZ) gene to provide an exon/intron splicing site and a polyadenylation signal. This chimeric gene was cut out from the vector, gel-purified, and microinjected into mouse eggs.

FIG. 4 shows the gene structure of the UPII/SV40 Tag transgene constructed by ligating a 3.6 kb 5'-flanking sequence of the UPII gene to a 2.8 kb SV40 Tag oncogene. The abbreviations for restriction sites are as in FIG. 1A and KpnI(K) and SpeI(Sp).

FIG. 5B shows the Southern results of representative F1 mice.

FIG. 6A is a H&E stained bladder section of No. 2 founder mouse, showing an invasive, papillary transitional cell carcinoma. FIG. 6B presents the same bladder as in FIG. 6A showing an area characteristic of carcinoma in situ. FIGS. 6C and 6D are immunofluorescent staining of bladder TCC with a pan-uroplakin antibody (FIG. 6C) and a rabbit antibody against SV40 T antigen (FIG. 6D). Note the nuclear staining of SV40 T antigen (FIG. 6D) and the membrane and cytoplasmic staining of uroplakins (FIG. 6C). FIG. 6E presents pelvic tumor mass (3 cm in diameter) in No. 29 founder mouse (inset), histologically showing a poorly differentiated tumor. FIG. 6F presents bladder epithelium of No.9 founder mouse showing changes typical of carcinoma in situ.

FIG. 10A is a H&E stained bladder section of No. 2 founder mouse, showing a pedunculated, superficial bladder tumor. The epithelium is markedly thickened with 10–20 cell layers with little atypia or mitoses. FIG. 10B is at higher magnification, showing pseudoglandular structure and neovascularization within the epithelial layer. FIGS. 10C and 10D present an assessment of ras expression in normal (FIG. 10C) and transgenic (FIG. 10D) mice by immunoperoxidase staining using a pan-ras antibody. Note a low level of endogenous ras expression in normal control mouse bladder (FIG. 10C), and a high level expression in the proliferating tumor cells of No. 2 transgenic mouse bladder. FIG. 10E is a H&E staining of a bladder section from an F1 mouse of No. 5 transgenic line, showing hyperproliferative changes of the urothelium.

FIG. 11B presents duplicate lanes blotted with a UPII antibody, showing equal gel loading.

DETAILED DESCRIPTION OF THE INVENTION

Figure 1A:
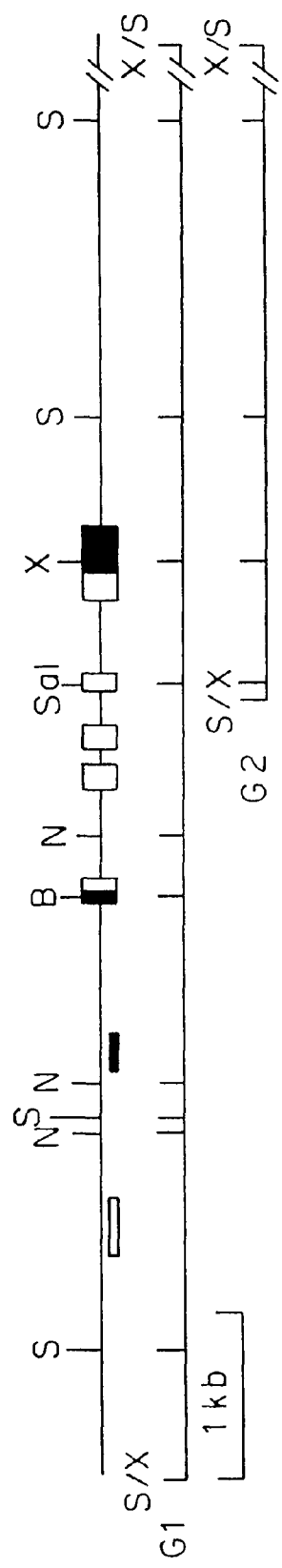

To define the role of genetic alterations in bladder cancer formation, a transgenic non-human mammal approach entailing the specific expression of oncogenes and mutated tumor suppressor genes in the urothelium through a uroplakin II promoter was developed by the present inventors using transgenic mouse as a first model system. It was found that the urothelial expression of SV40 Tag, which was shown previously to inactivate p53 and retinoblastoma (Rb) tumor suppressor genes, induced transitional cell carcinomas (TCC or alternatively designated as urothelial carcinoma) in the mouse urinary bladder. Transgenic mice harboring SV40 Tag first developed carcinoma in situ (CIS) and then progressed to invasive and metastatic TCCs, recapitulating the sequence of TCC development in humans. In another model, activated H-ras was overexpressed in mouse urothelium and differed from SV40 mice in that mice harboring activated H-ras exhibited urothelial hyperplasia which progressed to superficial, papillary TCCs. These changes again bear a striking resemblance to TCC formation and progression in human bladder cancer. Thus, SV40 and H-ras transgenic mice exhibiting distinct phenotypes that closely mimic the two distinct types of human bladder cancer show that these transgenic models, expressing well-defined genetic changes specifically in the bladder, are useful tools for understanding human bladder cancer formation.

The transgenic animals according to the present invention, serving as models for human bladder cancer, can be used to: (1) assess the tumorigenic potential of oncogenes and mutated tumor suppressor genes; (2) determine the cooperative effect among oncogenes and between oncogenes and tumor suppressor genes in bladder tumorigenesis; (3) study the sequence of bladder tumor development including the identification of pre-neoplastic lesion, tumor invasion and metastases; and (4) serve as a bioassay system for testing potential carcinogens. Furthermore, the transgenic animals according to the present invention provide in vivo models for testing preventative measures for bladder cancer as well as for testing novel therapeutic modalities including chemotherapy, radiation therapy, immunotherapy and gene therapy. In addition, the transgenic animals (and cells derived therefrom) according to the present invention can also be used to identify antineoplastic therapeutics such as anti-tumor agents, which act to decrease the proliferation of cells or the growth, dissemination, or metastasis of tumors, and chemopreventative agents, which act to inhibit the formation of new tumors.

To produce transgenic animals, any method known in the art for introducing a recombinant construct or transgene into an embryo, such as microinjection, cell gun, transfection, liposome fusion, electroporation, and the like, may be used. However, the most widely used method for producing transgenic animals, and the method most preferred according to the present invention, is microinjection, which involves injecting a DNA molecule into the male pronucleus of fertilized eggs (Brinster et al, 1981; Costantini et al, 1981; Harbers et al, 1981; Wagner et al, 1981; Gordon et al, 1976; Stewart et al, 1982; Palmiter et al, 1983; Hogan et al, 1986; U.S. Pat. Nos. 4,870,009; 5,550,316; 4,736,866; 4,873,191). The above methods for introducing a recombinant construct/transgene into mammals and their germ cells were originally developed in the mouse. These methods were subsequently adopted for use with larger animals, including livestock species (WO 88/00239, WO 90/05188, WO 92/11757; and Simon et al, 1988). Microinjection of DNA into the cytoplasm of a zygote can also be used to produce transgenic animals.

The present invention is not limited to any one species of animal, but provides for any appropriate non-human mammal species. For example, while mice is a preferred mammal species for producing transgenic animals, other non-limiting examples including guinea pigs, rabbits, pigs, sheep, etc., may be suitably used. The success rate for producing transgenic animals by microinjection is highest in mice, where approximately 25% of fertilized mouse eggs into which the DNA has been injected, and which have been implanted in a female, will develop into transgenic mice. A lower success rate has been achieved with rabbits, pigs, sheep and cattle (Jaenisch, 1988; Hammer et al, 1985 and 1986; Wagner et al, 1984).

The introduction of a DNA containing an oncogene or a tumor suppressing gene sequence at the fertilized oocyte stage ensures that the introduced gene will be present in all of the germ cells and somatic cells of the transgenic animal. The presence of the introduced gene in the germ cells of the transgenic "founder" animal in turn means that all of the founder animal's offspring will carry the introduced gene in all of their germ cells and somatic cells. Introduction of the gene at a later embryonic stage might result in the absence of the introduced gene in some somatic cells of the founder animal, but the offspring of such an animal that inherit the introduced gene will carry the gene in all of their germ cells and somatic cells.

There is no need for incorporating the gene being introduced into any kind of self-replicating plasmid or virus (Jaenisch, supra). In many cases, the presence of vector DNA has been found to be undesirable (Hammer et al, 1987; Chaka et al, 1985 and 1986; Kollias et al, 1986; Shani 1986; Townes et al, 1985). However, in order for the introduced gene sequence to be capable of being specifically expressed in the urothelium of the transgenic animal, the gene sequence must be operably linked to a urothelium-specific promoter.

A DNA molecule is said to be "capable of expressing" a protein if it contains nucleotide sequences which contain transcriptional and translational regulatory information, and such sequences are "operably linked" to nucleotide sequences which encode the protein. An operable linkage is a linkage in which the regulatory DNA sequences and the DNA sequence sought to be expressed are connected in such a way as to permit gene expression. The regulatory regions needed for gene expression in general include a promoter region as well as the DNA sequences which, when transcribed into RNA, will signal the initiation of protein synthesis. Such regions will normally include those 5'-noncoding sequences involved with initiation of transcription and translation. A promoter region would be operably linked to a DNA sequence if the promoter were capable of effecting transcription of that DNA sequence. Thus, the oncogene or tumor suppressing gene is operably linked to a urothelium-specific promoter to generate a recombinant construct or "transgene" that is then introduced into the fertilized egg.

The introduced gene sequence is an oncogene or a tumor suppressor gene that appears to be involved in bladder carcinogenesis. Preferred but non-limiting examples include the oncogenes, H-ras (Corominas et al, 1991b), Neu/erbB-2 (Yamamoto et al, 1986), c-myc (Stanton et al, 1984), SV40 Tag (Fiers et al, 1978), and the tumor suppressor genes, p53 (Zakut-Houri et al, 1983), p16 (Zhang et al, 1998) and Rb (Bernards et al, 1989).

Urothelium, also known as transitional epithelium, is a multilayered epithelium that covers the surface of much of the urogenital tract including the renal pelvis, ureter, the entire bladder and a portion of the urethra. The apical surface of urothelium, in direct contact with the urine, is covered with numerous rigid looking plaques. These plaques cover a large portion (>70%) of the apical surface of mammalian urothelium (Hicks, 1965; Koss, 1969, Staehelin, 1972). They are believed to play a crucial role as a permeability barrier (Hicks, 1975) and/or as physical stabilizer of the urothelial cell surface (Staehelin, 1972). When viewed in cross section, the outer leaflet of the plaque is almost twice as thick as the inner one, hence the term "asymmetrical unit membrane" or "AUM" has been used to describe these plaques.

It has recently been shown that AUM contain 4 major integral membrane proteins which are called uroplakin Ia (UPIa; 28 kDa), uroplakin Ib (UPIb; 27 kDa), uroplakin II (UPII; 15 kDa) and uroplakin III (UPIII; 47 kDa). EM-immunolocalization studies established that these uroplakins are AUM-associated in situ, thus establishing them as the major protein subunits of urothelial plaques (Yu et al, 1990; Wu et al, 1990). Immunohistochemical survey of various bovine tissues established that these UPs are urothelium-specific, being present in the upper cell layers of the urothelia that cover the urogenital tract including the renal pelvis, ureter, bladder and part of the urethra. These data established uroplakins as excellent markers for an advanced stage of urothelia differentiation (Yu et al, 1990; Wu et al, 1990). Furthermore, uroplakins Ia, Ib, II and III form the major protein components of all mammalian urothelial plaques. They are found in eight other mammalian species (human, monkey, sheep, pig, dog, rabbit, rat, and mouse), and the AUMs of these species appear morphologically similar, bearing crystalline patches of 12-nm protein particles with a center-to-center spacing of 16.5 nm (Wu et al, 1994).

The primary structures of UPs have recently been elucidated by cDNA cloning. The results established the existence of two closely related UPI isoforms, the 27-kDa UPIa and the 28-kDa UPIb (Yu et al, 1994). The mRNAs of all four known UPs have recently been shown to be urothelium-specific, indicating that expression of UP genes is transcriptionally regulated (Yu, 1994; Lin et al, 1994; Wu et al, 1993).

The expression of the mouse UPII gene, like its bovine counterpart, is urothelium- and late-differentiation stage-specific. Using transgenic mouse techniques, a 3.6-kb 5' flanking region has now been identified as a promoter comprising the cis-elements for directing the expression of a heterologous reporter gene (LacZ) specifically and efficiently to the suprabasal cell layers of the urothelium in a manner similar to the endogenous UPII gene. The high level of LacZ expression in the urothelium was found to be independent of chromosomal integration sites and directly proportional to the transgene copy number in the transgenic mouse.

Experiments have also been performed wherein the uroplakin II promoter was used to drive the expression of the biologically active human growth hormone gene in the urothelium of transgenic mice. In these experiments, a vector was constructed with the 3.6-kb UPII promoter placed upstream from a human growth hormone cDNA. The vector was then injected into the fertilized mouse eggs for transgenic mouse production. Thirteen founder mice were generated. Of these, six (5 male and 1 female) transmitted the transgene to their offspring. Immunofluorescence staining of the bladder epithelium of these transgenic mice using antibodies to hGH showed strong staining indicating high level of expression. Immunolocalization performed by high resolution electron microscopy showed the accumulation of electron dense, aggregates of hGH that are labeled by immuno-gold particles conjugated with antibodies to hGH. Most of the hGH particles are found in the vesicles lined with the asymmetrical unit membrane that are normally involved in transporting the uroplakins to the apical surface of the bladder epithelium. In addition, some of the hGH particles formed another distinct population of cytoplasmic vesicles thus revealing the presence of a previously unrecognized secretory pathway that may normally operate at a low level in bladder epithelium. The high level of overexpression of hGH makes these vesicles easily visible.

Urine from these mice was collected and hormone levels determined by radioimmunoassay. Many of the F1 offspring had a significant level of human growth hormone in their urine (up to 300 ng/ml), thus demonstrating that the biologically active molecule was secreted into the urine. Further, blood concentrations of the hormone were less than 5 ng/ml indicating that the synthesized hormone is secreted vectorially into the bladder cavity rather than into the bloodstream.

Other urothelia closely related to the epithelium of the bladder known to cover other areas of the urinary tract, such as the renal pelvis of the kidney, the ureter, and the urethra and which also elaborate AUM plaques, exhibit similar expression of the transgene.

These data show that a promoter active in directing expression in the urothelium of an animal, such as the 3.6-kb 5'-flanking sequence of the mouse UPII gene, can drive both a heterologous reporter gene and a gene for a biologically active molecule to express in the upper cell layers of the bladder epithelium. The lack of expression in non-urothelial tissues indicates a high degree of tissue-specificity and demonstrates that the cis elements of this promoter region provide very tight regulatory control on tissue-specific and differentiation-dependent expression of a gene placed downstream of the promoter. As these results were corroborated in independent transgenic lines with differing sites of transgene integration, they show that the inherent promoter activity is responsible for the tissue-specific expression and is not due to the effect of neighboring sequences of the transgene integration sites.

It has also been found by the present inventors that a urothelium specific promoter can direct expression of a human oncogene to the urothelium and is useful in the production of animal models for human bladder cancer. In these experiments, a chimeric gene comprising a 3.6 kb 5'-flanking sequence of mouse uroplakin II gene and a 2.8 kb SV40 Tag oncogene was constructed. This chimeric gene was then microinjected into fertilized mouse eggs which were implanted into foster mothers to produce transgenic mice expressing the oncogene. Four transgenic founder mice carrying uroplakin II/SV40 Tag chimeric genes were identified from thirty live births. Two of these positive founder mice harboring 10 and 6 copies of transgenes succumbed with bladder tumors at ages of 3 and 5 months, respectively. Histological examination revealed tumors that were invasive transitional cell carcinomas, resembling those occurring in humans. RT-PCR confirmed the expression of SV40 Tag oncogene in urothelial tumors, but not in non-urothelial, normal tissues. Immunohistochemical staining showed the typical nuclear staining of SV40 Tag in bladder tumor cells. The remaining two transgenic mice carried lower copy number of transgenes and exhibited a urothelial morphology resembling carcinoma in situ as is seen in humans. In contrast, no tumors were seen in over 50 transgene negative mice.

While all of the experiments discussed above were conducted using the mouse UPII promoter, other promoter constructs capable of directing urothelial gene expression can be used to yield similar results as will be obvious to those of skill in the art. For example, mouse uroplakin II 5'-upstream sequences which are shorter or longer than 3.6-kb but which can still achieve the same degree of urothelium expression, can be used. Also useful are DNA sequences with relatively minor modifications to the mouse UPII promoter, such as sequences with point mutations, partial deletions or chemical modifications.

In addition, sequences that are related to the 3.6 kb 5' flanking sequence of the mouse uroplakin gene, including, but not limited to, promoter sequences of uroplakin-II-homologous genes of other mammalian species such as human, cattle, sheep, goat, rabbit and rat, can also be used. There is sufficient similarity between this gene in different species, so that similar results with the UPII promoter sequence in other animals is expected. For example, the UP gene organization (Ryan et al, 1993), cDNA (Lin et al, 1994) and protein sequences, tissue patterns of expression, and morphology of AUMs are strikingly similar between the mouse and cow. The amino acid sequence of bovine and mouse UPII are highly similar, sharing 84 of their 100 amino acid residues (Wu et al, 1994). In addition, although the onset of expression of the UPII gene is different in these two species, UPII is clearly differentiation-related in both cow and mouse urothelia.

Further, promoters of other genes that are active in directing expression in the urothelium are known and can also be used according to the present invention. Examples include, but are not limited to, the promoter of uroplakin 1a (Yu et al, 1994); Yu et al, 1990), uroplakin Ib (Yu et al, 1994; Yu et al 1990), uroplakin III (Wu et al, 1993), and the urohingin gene (Yu et al, 1992).

Identification of additional promoters active in directing gene expression in the urothelium can be routinely performed using the subtraction library technique. Using this technique which eliminates the cDNAs that are shared by multiple tissues (Diatchenko et al, 1996), a library highly enriched in bladder specific cDNAs was generated. Total RNAs were isolated from stomach, intestine, colon, liver and brain. Northern blot analysis of these mRNAs using an actin cDNA as a probe demonstrated the intactness of the actin mRNA in all of these preparations. Bladder cDNAs were then used as the "tester", and the cDNAs of all the other non-bladder tissues, referred to as the "drivers" were subtracted from the bladder cDNAs. The cDNAs of the non-subtracted and the subtracted were probed using actin cDNA or uroplakin Ib. The results indicate that the original bovine bladder cDNA preparation contained abundant actin mRNA and relatively little uroplakin Ib mRNA. In contrast, the subtracted library contained almost no detectable actin mRNA (at least 50 fold reduction) but greatly increased uroplakin Ib mRNA (>10 to 15 fold enrichment). Multiple cDNA clones have been isolated from the subtraction library and used to probe the mRNAs of various bovine tissues. For example, a uroplakin Ib probe confirmed its bladder specificity. Tissue distribution patterns have also been determined for three unidentified partial cDNAs which are relatively bladder specific. Sequencing data indicate these three clones are novel genes not described previously. It is believed that the promoters of these genes will also be useful in directing expression of a heterologous gene for a biologically active molecule in the urothelium of transgenic animals.

By crossbreeding and inbreeding the transgenic non-human animal according to the present invention, as well known in the art, the offspring may be heterozygous or homozygous for the transgene or can be bi-transgenic (carrying two different transgenes). For example, transgenic mice heterozygous for a transgene of a tumor suppressor gene, such as p53, can be bred to produce transgenic mice homozygous for the mutant tumor suppressor transgene, which then doubles the transgene dosage, possibly hastening the functional inactivation of the endogenous wild-type tumor suppressor gene in the transgenic homozygote.

For in vivo cooperativity of oncogenes and tumor suppressor genes in the urothelium, two transgenic mice harboring different transgenes can be crossbred to deliver two well-defined genetic changes to a bi-transgenic offspring.

DNA analyses of the resulting crossbred offsprings can reveal which offsprings harbor both transgenes. Accordingly, a variety of different bi-transgenic animals can be produced by crossbreeding different combinations of single-transgene-carrying transgenic animals. Furthermore, a bi-transgenic animal may be crossbred with another transgenic animal to produce tri-transgenic animals, which may in turn be mated to other transgenic animals, and so forth in order to produce animals carrying a multiplicity of transgenes. Multi-transgenic animals harboring more than one type of transgene may also be produced by co-injecting (or otherwise introducing) multiple transgenes into the fertilized egg.

Having now generally described the invention, the same will be more readily understood through reference to the following examples which are provided by way of illustration and are not intended to be limiting of the present invention.

EXAMPLE 1

Characterization of the Mouse UPII Gene

Figure 1B:
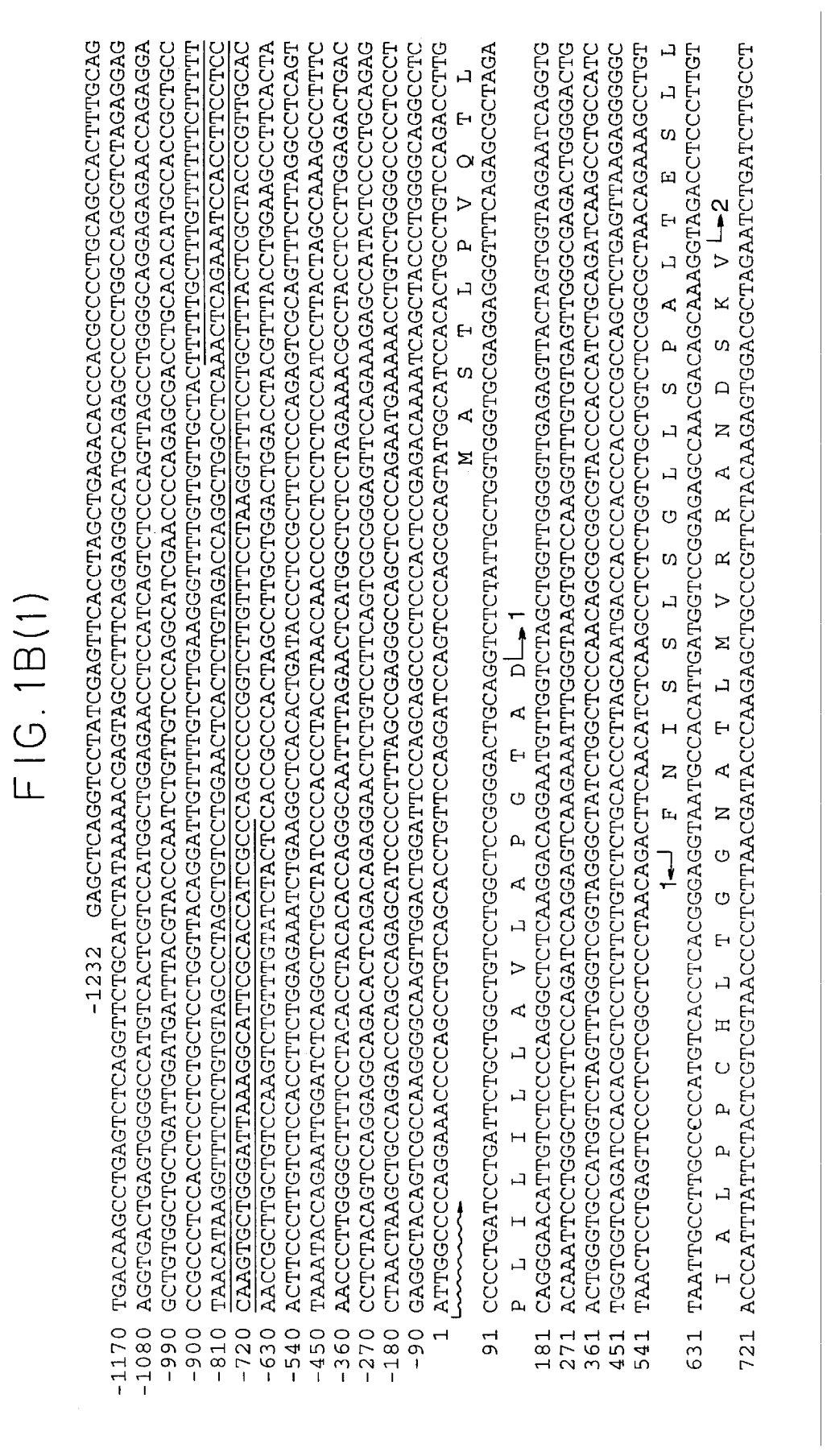

A bovine UPII cDNA (Lin et al, 1994) was used as a probe to screen a mouse EMBL3-SP6A/T7 genomic library (Clontech Laboratories Inc., Palo Alto, Calif.). Two overlapping clones (G1 and G2) were isolated (FIG. 1A) and were sequenced by the dideoxynucleotide termination method. The transcriptional initiation site was determined by sequencing three clones of 5'-RACE (rapid amplification of cDNA ends) products of mouse bladder cDNA. The 16-kb mouse genomic clone (G1) contains an ≈2.5-kb transcribed region that is flanked by ≈3.5-kb and ≈10 kb of 5'- and 3'-sequences, respective (FIG. 1A). Alignment of the coding sequences with the UPII cDNA sequences of cattle (Lin et al, 1994), which are highly homologous, defined the exon/intron junctions of four introns (FIG. 1B). 5'-RACE (Frohman et al, 1988) experiments using mouse bladder mucosal mRNA as a template established that the transcription site of the UPII gene is located at 60-bp 5'-upstream of the translation initiation codon and 27-bp downstream of a putative TATA box. The 5'-upstream region contains an Alu-like B1 repetitive sequence (−830 bp) and a $(CA)_n$ stretch (≈−2.1 kb). Finally, a polyadenylation signal resides ≈230 bp downstream of the translation stop codon (FIG. 1B).

Figure 2:
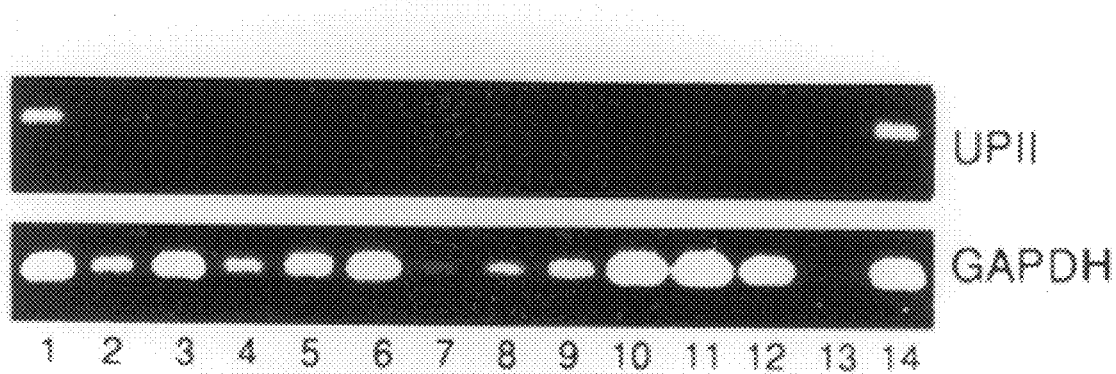
FIG. 2 illustrates the tissue distribution of UPII mRNA as assayed by reverse transcriptase polymerase chain reaction (RT-PCR). Poly(A)+mRNAs (0.3–0.4 mg) from mouse bladder (lanes 1 and 13), skin (2), forestomach (3), glandular stomach (4), kidney (without renal pelvis) (5), liver (6), spleen (7), testis (8), and thalamus/hypothalamus (9), cerebral cortex (10), and cerebellum (11) regions of the brain were reverse-transcribed, and amplified with either UPII-specific primers (Upper; 266 bp) or glyceraldehyde-3-phosphate dehydrogenase (GDH)-specific primers (Lower, as an internal control for comparison; 130 bp). The polymerase chain reaction (PCR) products were then electrophoresed on a 1.3% agarose gel and stained with ethidium bromide. Lane 12 is a negative control (no cDNA template). The 266-bp UPII product was detected in abundance in bladder, but not in any other tested tissues, including the hypothalamus.

The mouse UPII gene is also expressed in the urothelium. Messenger RNAs were prepared from various mouse tissues and probed for the presence of UPII sequences by RT-PCR assay. A large amount of UPII product of expected size (266-bp) was generated from the bladder, but not from skin, forestomach, glandular stomach, kidney, liver, spleen, testis, or the hypothalmus/thalmus cortex and cerebellum of the brain (FIG. 2).

EXAMPLE 2

Expression of a Fusion Gene (UPII-LacZ) in Transgenic Mice

Figure 3A:
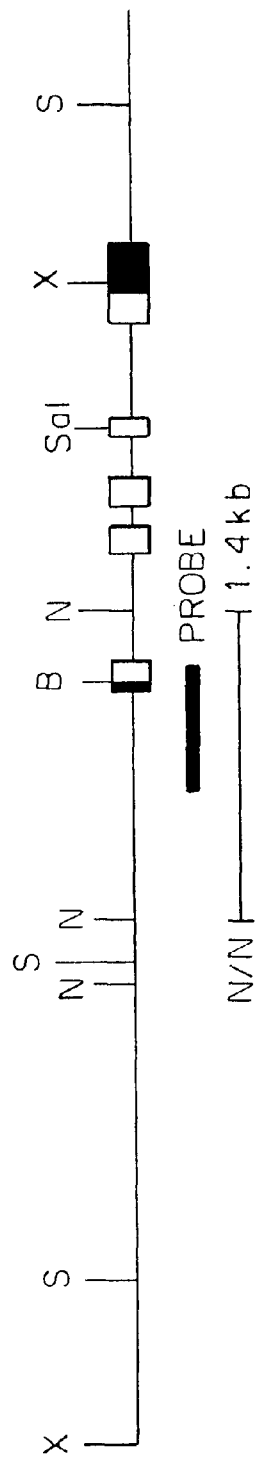
FIGS. 3A and 3B illustrate the construction and quantitation of a representative transgene.
Figure 3B:
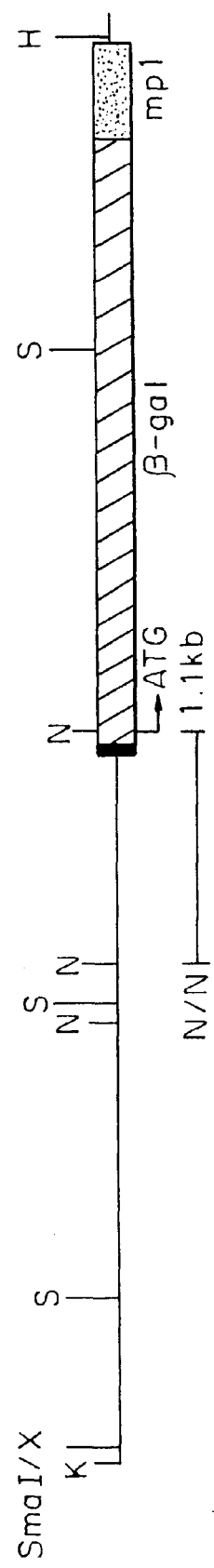

To define the cis promoter elements for urothelial-specific expression and to demonstrate that heterologous genes can be targeted to the suprabasal urothelial cells as endogenous UPII, a transgenic mouse was constructed that contains a chimeric gene in which a LacZ reporter gene was under the regulation of a 3.6-kb 5'-flanking sequence of the mouse UPII gene (FIG. 3B).

A 6-kb XhoI DNA fragment of the G1 genomic clone (FIG. 1A) was sub-cloned in pGEM7Z and then restriction-cut to yield a 3.6-kb DNA fragment of G1 clone (extending from the XhoI site at −3.6 kb to the BamHI site at −42 bp relative to the transcription initiation site) and inserted into the SmaI site of a LacZ vector, placF, (Peschon et al, 1987); Mercer et al, 1991) to generate pUPII-LacZ (FIG. 3B). The 7.1-kb fusion gene was excised using KpnI and HindIII, gel-purified, and microinjected into fertilized mouse eggs (from F1 hybrids of C57BL/6J X DBA2), which were implanted into CD-1 foster mothers. The LacZ transgene was identified by Southern blot analysis of tail DNA in accordance with methods well known in the art. Southern blot analyses of the tail DNAs showed that the transgene was integrated into the genomes of 4 of 25 mice. Three of these animals transmitted the reporter gene to their progeny. Southern blot analyses further established that the genomic DNAs of these three transgenic lines, TG1, TG2, and TG3, contained roughly 40, 6, and 30 copies, respectively, of the reporter gene per diploid genome. Probing the same Southern blot with the LacZ sequence showed that the transgenes of all three lines were in tandem repeats and were integrated into independent sites.

In all three mice lines, the transgene was expressed in the suprabasal cells of the bladder epithelium in an expression pattern similar to the endogenous UPII gene. The staining correlated somewhat with gene dosage, as it was intense in TG1 (40 copies) but moderate in TG2 (6 copies) and TG3 (30 copies). β-galactosidase activity was only observed in the bladder and other urothelia of mice that had inherited the transgene, confirming that the activity was transgene-specific. In all three transgenic mice, no β-galactosidase activity was detected in any of the non-urothelial stratified epithelia tested, including those of the skin, tongue, cornea, esophagus, and forestomach. The reporter gene product was also undetectable in all other epithelia tested, including those of liver, lung, glandular stomach, small and large intestine, uterus, and testis; or mesenchymal tissues, including fibroblasts, endothelial cells, spleen, and various muscle cells. Positive founder animals were back-crossed with (C57BL/6J X DBA2) F1 hybrids to generate semizygous animals that were used for studying transgene expression.

EXAMPLE 3

Transgenic Mice Expressing SV40 T Oncogene Develop Carcinoma in Situ and Invasive Cancers of the Bladder Generation of Transgenic Mouse Lines Expressing the SV40 Tag in Urothelium: The uroplakin II-SV40 T chimeric gene was constructed by fusing murine uroplakin II gene promoter with the coding sequences of SV40 large T oncogene. Briefly, a 3.6 kb KpnI-BamHI fragment containing the UP II promoter was sub-cloned into pBluescript KS+ (Stratagene, La Jolla, Calif.; Lin et al, 1995). The BamHI site downstream of the UPII promoter was used to clone a 2.8 kb BamHI fragment containing the SV40 large T oncogene (FIG. 4). The UPII-SV40 T transgene orientation was confirmed by restriction digestion, by PCR using a sense primer located in the UPII promoter and an antisense primer in the SV40 T oncogene, and by DNA sequencing of the junction region.

The 6.4 kb fusion gene (UPII/SV40 T transgene) was excised en bloc from pBluescript SK+ cloning vector (Stratagene) by restriction digestion with KpnI and SpeI. After agarose gel electrophoresis and column purification, the transgene was microinjected into the pronuclei of fertilized eggs of FVB/N inbred mice for transgenic mouse production (Hogan et al, 1986). The injected eggs were implanted into four pseudopregnant FVB/N mice which gave birth to a total of 30 pups.

Southern Blotting of Mouse Tail Genomic DNA:

Transgene incorporation in founder animals was determined by Southern blot analysis. Briefly, mouse tail DNA was digested with NotI and probed with a $^{32}$P-labeled, fragment PstI(500 bp) from the SV40 T oncogene. For the estimation of transgene copy number, 600 bp BamHI-StuI fragment of UPII promoter was used as a probe to detect endogenous genes, as well as transgenes. The X-ray film of genomic Southern blot was subjected to densitometry for the calculation of the relative amount of transgenes.

Figures 5A, 5B:
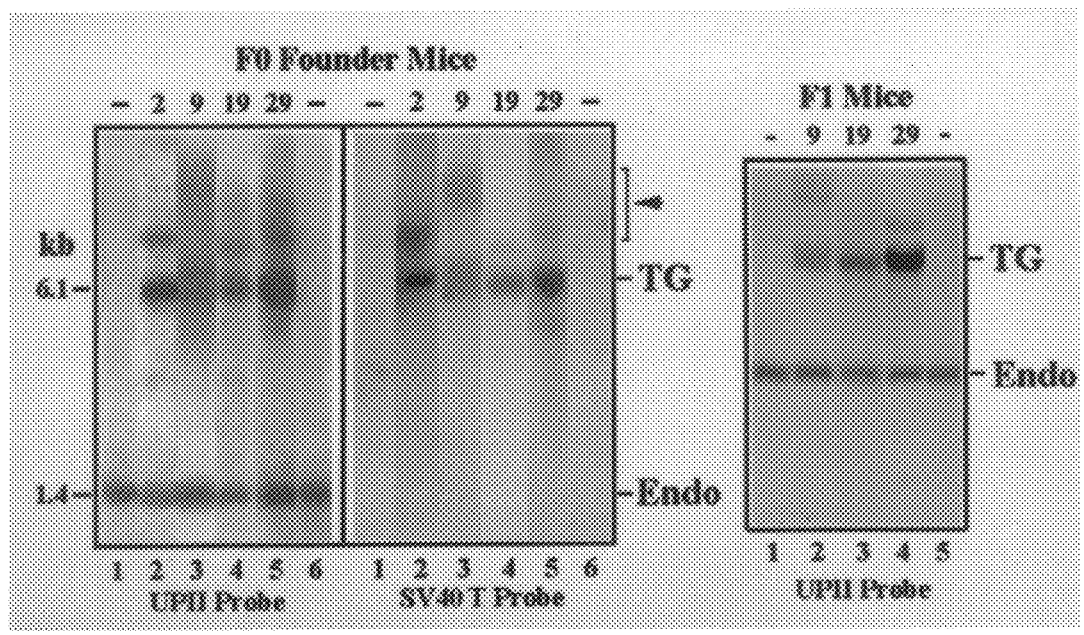
FIGS. 5A and 5B show the identification of mUPII/SV40 Tag-transgenic mice by Southern blotting. Mouse tail DNAs were digested with NcoI and probed with UPII and SV40 Tag probes, P1 and P2, respectively, as indicated in FIG. 4. Note that four FO founder mice (Nos. 2, 9, 19 and 29) in FIG. 5A contain a 6.1 kb transgene (TG) which hybridized with both probes. A 1.4 kb endogenous UPII gene fragment (Endo) reacted with the UPII probe, but not the SV40 probe. Note the generation of two lines (2 and 29) with high transgene copies and two lines (9 and 19) with low copies. Two negative mice (-) were included in each panel as controls. Arrow shows the varied lengths of the last copy of transgene flanking the genome sequences.

Southern blotting analysis of tail DNAs indicated that four mice had incorporated the UPII/SV40 T transgene into their genome (FIG. 5A). The transgenes of all four mice were inserted in tandem repeats. However, the amount of transgene incorporation in these four founder mice was different. Founders 2 and 29 harbored 10 and 6 copious of transgenes respectively, while founders 9 and 19 each harbored only 2 copies. Southern blotting of F1 mouse DNAs showed that with the exception of founder 2, all other founder mice transmitted the transgenes to their progenies (FIG. 5B).

Histological, Immunohistochemical and Immunoflorescent Staining: Freshly dissected mouse tissues were fixed in 10% buffered formalin and embedded in paraffin. 3–5 µm thick sections were then stained with hematoxylin and eosin and examined microscopically for pathological changes. For the staining of SV40 large T antigen, paraffin sections were digested with 0.25% trypsin in 25 mM Tris/HCl, pH 7.8 at 37° C for 15 min., and incubated with a rabbit antiserum against large T antigen (obtained from Douglas Hanahan of University of California, San Francisco). After washing in phosphate-buffered saline, the sections were incubated with a goat anti-rabbit antibody conjugated with horseradish peroxidase and developed in a diamine benezidine/$H_2O_2$ solution. For retrieval of uroplakin antigens, paraffin sections were microwaved in citrate buffer, pH 6.0 for 15 min. These sections were then stained with a rabbit pan-uroplakin antibody followed by a peroxidase-conjugated secondary antibody. For immunofluorescent staining, tissue blocks were fixed in Zamboni's solution (2% paraformaldehyde plus 15% picric acid) and embedded in OCT compound. 5 µm thick cryosections were then stained by indirect immunofluorescent methods.

Analysis of Phenotypic Changes of mUPII/SV40 T Mice: the phenotypic changes of the four transgenic founder mice were slightly different, most likely due to the level of SV40 Tag expression as shown in Table 1.

TABLE 1

Summary of mUPII/SV40 T Transgenic Mice

| mUPII/SV40 T Lines | TG Copy Number | Breeding Stage | Bladder Histology |
|---|---|---|---|
| No. 2 | 10 | $F_0$ | Invasive TCC |
| No. 9 | 2 | $F_0$ | CIS |
|  |  | $F_1$ | CIS |
|  |  | $F_2$ | N/D |
| No. 19 | 2 | $F_0$ | CIS |
|  |  | $F_1$ | CIS |
|  |  | $F_2$ | N/D |
| No. 29 | 6 | $F_0$ | Metastic TCC |
|  |  | $F_1$ | CIS |
| Neg. Control | 0 | $F_2$ | Normal Urothelium |

Figure 6A:
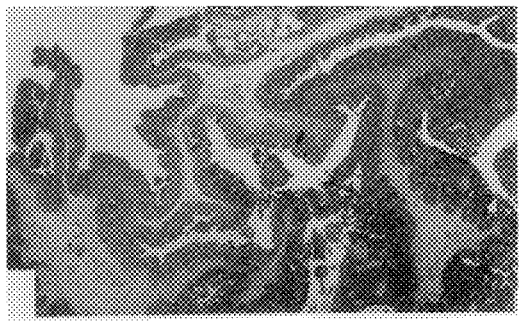
FIGS. 6A–6F show histopathological analyses of mUPII/SV40 Tag transgenic mice.
Figure 6B:
Figure 6C:
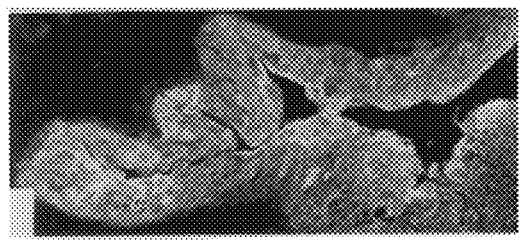
Figure 6D:
Figure 6E:
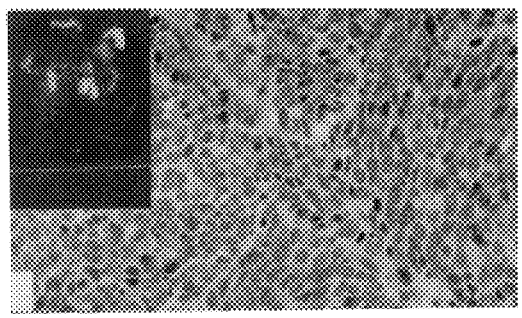

The two founder mice carrying high copy numbers of transgenes (F0.2 and F0.29) succumbed with bladder cancer at the ages of 3 and 5 months, respectively. By histology, F0.2 mouse developed a moderately differentiated transitional cell carcinoma that had invaded into the detrusor muscle layer (FIG. 6). Interestingly, patches of urothelial cells whose basement membrane remained intact had severe atypia with marked nuclear pleomorphism, including giant nuclei and frequent mitotic figures, closely mimicking carcinoma in situ (CIS) (FIG. 6B). This suggests a possible sequence of tumor progression from CIS to invasive phenotype in this SV40 Tag-expressing mouse (also see below). F0.29 mouse developed an abdominally palpable tumor at 5 months of age. Upon inspection of the anatomy, a tumor mass measured 3 cm in diameter occupied the entire pelvic region and encompassed pelvic organs, including the bladder, prostate, seminal vesicles and colon (FIG. 6E, inset). Distant metastasis to lingular lobe of the liver was also visible. Histological survey of the tumor showed a poorly differentiated TCC composed of dense anaplastic cells with scant cytoplasm (FIG. 6E). Micrometastases were confirmed in the lingular lobe of the liver.

Since uroplakins are also expressed in renal pelvis and ureters (Lin et al, 1995), the UPII gene promoter could direct SV40 Tag to express in these parts of the urinary tract. The stage of tumor development in renal pelvis and ureters of the F0.2 and F0.29 mice was therefore studied. Although both mice developed full-blown bladder cancers, their renal pelvis and ureters exhibited changes characteristic of CIS, suggesting an earlier tumor stage in these areas. The underlying mechanisms for advanced tumor stage in the bladder, but relatively early tumor stage in the renal pelvis and ureters of these transgenic mice are currently unclear, but they may be related to prolonged exposure of bladder urothelium to secondary urinary carcinogens.

Figure 6F:
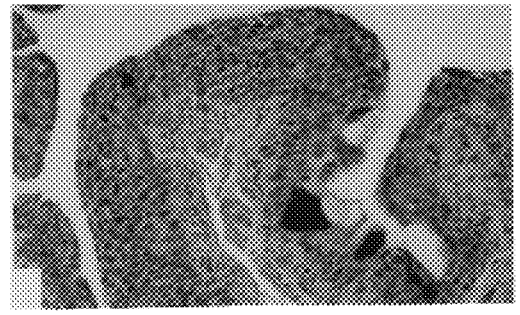

Unlike the development of outgrown bladder tumors in mice harboring a high copy number of SV40 Tag transgenes, mice harboring low transgenes copies (F0.9 and F0.19) remained apparently healthy. Histological analysis of bladders from 7–9 month-old, transgene-positive mice consistently showed moderate to severe urothelial atypia with CIS morphology (FIG. 6F). Taken together, these results suggest that the stage of bladder tumor development and progression in these mice is transgene dose-dependent, thus offering a unique opportunity to dissect the sequential steps of tumor formation. Since mice carrying low copy number of transgenes have a much more insidious process of tumor development, they serve as important tools for studying the cooperative nature of different oncogenes.

Isolation of RNA, Reverse-Transcription and Polymerase Chain Reaction: Expression of SV40 Tag mRNA in transgenic mouse tissues was assessed by RT-PCR. Total RNA was extracted from normal and transgenic mouse bladders and from bladder tumor tissues using an RNA extraction kit (Promega). 1 µg of total RNAs from each preparation was reverse-transcribed into cDNAs with an oligo-dT primer. Portions of the cDNAs were subjected to PCR using a sense and an antisense primer located in the first and second exons of SV40 T oncogene. These two primers were so designated that the amplification of SV40 mRNA would yield a 400 bp PCR product, while the amplification of precursor mRNA and genomic DNA contamination of total RNA preparation would yield a 740 bp product.

Figure 7:
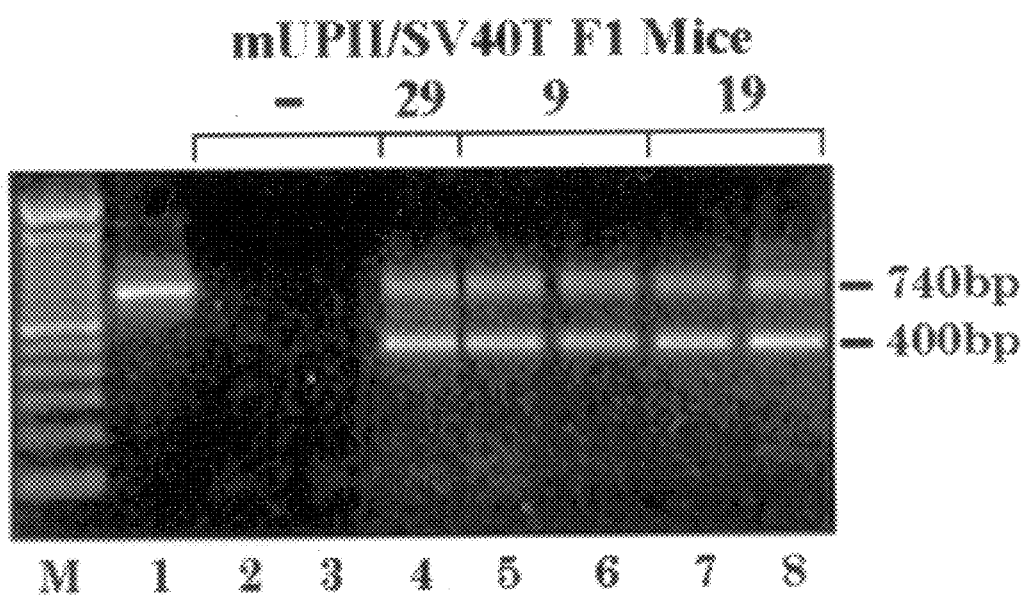
FIG. 7 shows a RT-PCR analysis of SV40 Tag mRNA in mouse bladders on agarose gel electrophoresis. Total RNAs were extracted from the urinary bladders of F1 mice and subjected to RT-PCR using two primers located in two different exons of SV40 Tag gene. Note a 400 bp SV40 Tag gene product in all transgene-positive mice (lanes 4–8), but not in transgene-negative mice (lanes 2 and 3). The 740 bp band corresponds to SV40 Tag genomic sequence containing an intron, due to genomic DNA contamination in RNA preparations. Lane 1 shows the PCR control in which transgene constructs were used as a template.

Correlation of Tumor Formation with SV40 Tag Expression: The above neoplastic changes that were observed occurred exclusively in mice expressing SV40 Tag in the urothelium; none of the 26 transgene-negative mice that were analyzed had urothelial abnormality. To establish the correlation between SV40 Tag expression and neoplastic transformation, the presence of SV40 Tag in tumor tissues was studied. By isolating RNAs from tumor tissues followed by RT-PCR assay, as described above, SV40 Tag mRNA was found to be expressed in bladder tumor tissues of transgenic mice, but not in normal bladder epithelium of transgene-negative mice (FIG. 7). Immunohistochemical staining using a rabbit anti-SV40 Tag antibody revealed a typical nuclear staining of SV40 Tag in almost all tumor cells (FIG. 6D). In addition, antibodies against uroplakins stained SV40 Tag-positive tumor cells, albeit at a lower level than the normal urothelial cells (FIG. 6C). This latter finding is consistent with previous studies in the laboratory of the present inventors showing that the majority of human TCCs retained uropolakins (Moll et al, 1995; Wu et al, 1997).

Significance of the mUPII/SV40 Tag Transgenic Mice: The generation of an SV40 Tag bladder cancer model is significant in several aspects. First, it demonstrates the feasibility of the transgenic approach using the murine UPII gene promoter. Second, so far only transitional cell carcinomas, but not adenocarcinoma or squamous cell carcinoma have been produced from these mice, suggesting that this mouse model mimics the human occurrence. Third, the formation of CIS and invasive TCCs, instead of superficial papillary TCC in this model supports the notion that the inactivation of p53 and Rb (by the large T antigen) is largely responsible for the aggressive type of bladder cancer. Fourth, with this model, changes and the mode of tumor progression can now be identified and dissected by following urothelial changes in a temporal manner, i.e., in different ages of mice. Finally, although mice harboring low copy numbers of the transgenes may have a longer latency period for developing late stage tumors, they serve as an excellent model for assessing the synergism of other oncogenes and carcinogens.

EXAMPLE 4

Transgenic Mice Harboring Activated H-ras Oncogene Induced Urothelial Hyperplasia and Superficial Papillary Tumor of the Bladder Although H-ras is perhaps the only known oncogene whose mutations are consistently identified in a significant portion of human bladder cancer, its biological potential in inducing bladder tumor formation is unclear (Knowles, 1995). To target the urothelial expression of an activated H-ras, a fusion gene composed of the murine UPII gene promoter and an activated c-H-ras was constructed. A 3.0 kb c-H-ras gene, initially isolated from rabbit keratoacanthoma, harbors a point mutation at codon 61 of the second exon (Corominas et al, 1991a). The mutation is an A:T to T:A transversion that changes the codon CAG (encoding glutamine) to CTG (leucine). This activated c-H-ras(61L) was shown previously to be able to transform cultured NIH 3T3 cells (Corominas et al, 1991a).

Figure 8:
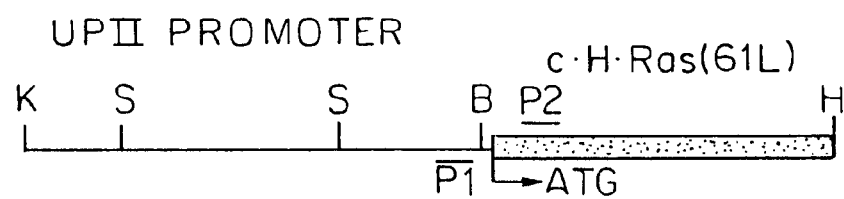
FIG. 8 illustrates a transgene construct (mUPII/c-H-ras) composed of a 3.6 kb murine UPII promoter and a 3.0 kb rabbit c-H-ras harboring a point mutation at codon 61. P1 and P2 denote the two DNA probes for Southern blotting analyses to detect the transgenes in FIG. 9.

Construction of Transgene: The uroplakin II-H-ras chimeric gene (transgene) was constructed by fusing murine uroplakin II gene promoter with a rabbit H-ras oncogene harboring a point mutation at codon 61 (61L), using the pUPII-LacZ as a host vector (Lin et al, 1995). Briefly, a 2.7 kb EspI H-ras gene fragment was derived from the pK10Hras13 construct previously described by Corominas et al (1991a), blunt-ended with Klenow enzyme and subcloned onto the SmaI site in pBluescript KS+(Stratagene, La Jolla, Calif.). This H-ras fragment was excised out with BamHI and HindIII and cloned into the corresponding sites of pUPII-LacZ to replace the LacZ gene. The UPII-H-ras transgene orientation was confirmed by restriction digestion, by PCR using a sense primer located in UPII promoter and an antisense primer in H-ras oncogene, and by DNA sequencing of the junction region. The 6.3 kb UPII-H-ras chimeric gene was excised en bloc from the cloning vector by restriction digestion with KpnI and HindIII (FIG. 8). After agarose gel electrophoresis and column purification, the chimeric gene fragment was microinjected into the pronuclei of fertilized eggs of FVB/N inbred mice for transgenic mouse production, as previously described (Hogan et al, 1986).

Southern Blotting of Mouse Tail Genomic DNA: For the assessment of the in vivo tumorigenic potential of this H-ras activation, the mUPII/c-H-ras transgene was used for transgenic mouse production as described above. Transgene incorporation in founder animals was determined by Southern blot analysis. Briefly, mouse tail DNA was digested with SacI and probed with a $^{32}$P-labeled, BamHI-NcoI(600 bp) fragment from rabbit H-ras oncogene. For the estimation of transgene copy number, a 600 bp BamHI-StuI fragment of UPII promoter was used as a probe to detect endogenous genes, as well as transgenes. The X-ray film of genomic Southern blot was subjected to densitometry for the calculation of the relative amount of transgenes.

Figure 9:
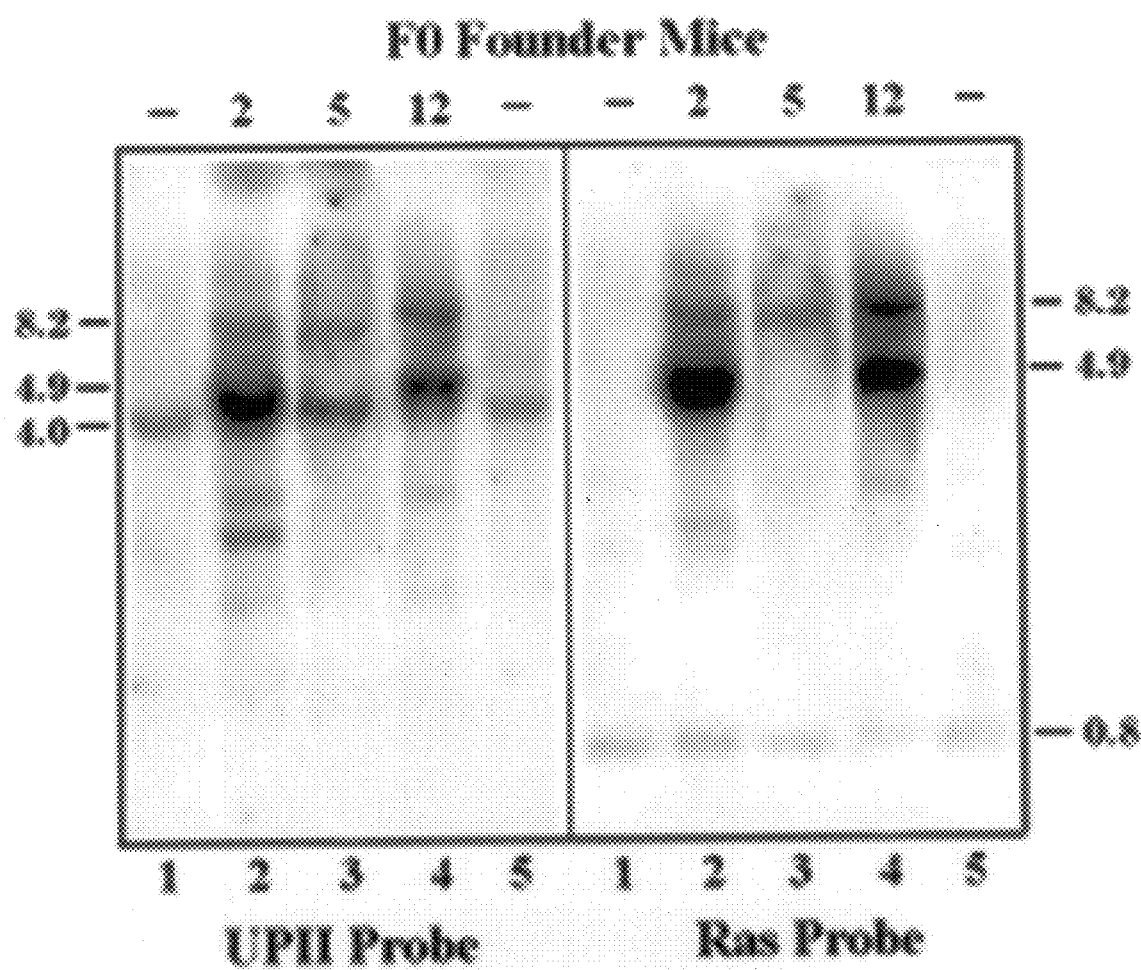
FIG. 9 shows Southern blotting analyses of the integration of mUPII/c-H-ras (61L) transgene in founder mice. Mouse tail DNAs were digested with SacI, electrophoresed, transferred to nylon membrane and hybridized with either a mouse UPII probe (P1 in FIG. 8) or a rabbit ras probe (P2). Note the detection of a 4.9 kb and an 8.2 kb transgene fragments in founders 2 and 12, but only an 8.2 kb transgene fragment in founder 5. These two different-sized transgene fragments belong to a "head-to-tail" and a "tail-to-tail" transgene orientation, respectively. The 4.0 kb band corresponds to the endogenous UPII fragment. The 0.8 kb band detected by the ras probe represents the endogenous mouse ras fragment. Transgene-negative mice (lanes marker with −) were used as controls.

Of the 20 live-born mice, three integrated the transgenes in the genome. Using both UPII and ras probes, two restriction fragments (4.9 kb and 8.2 kb) were detected in founder mice 2 and 12 on Southern blots, but only one in founder 5 (FIG. 9). Based on restriction mapping, these two different-sized restriction fragments correspond to a "head-to-tail" and a "tail-to-tail" transgene orientation, respectively. In addition, the three founder mice harbored 10, 4 and 2 copies of transgenes, respectively (FIG. 9).

Figure 10A:
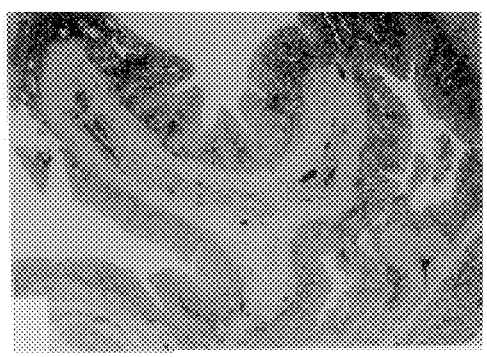
FIGS. 10A–10E show histopathological analyses of mUPII/c-H-ras (61L) transgenic mice.
Figure 10B:
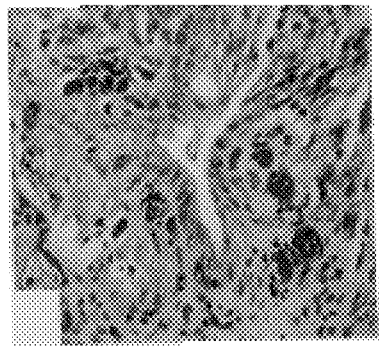
Figure 10C:
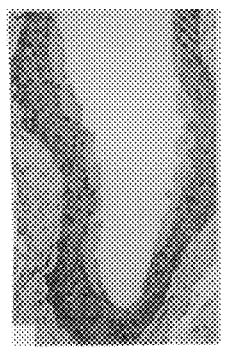
Figure 10D:
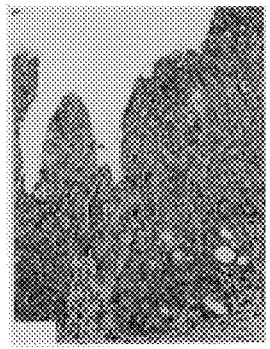
Figure 10E:
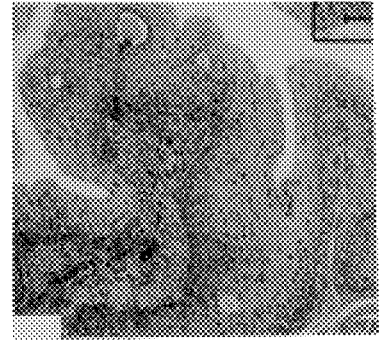
Figure 11:
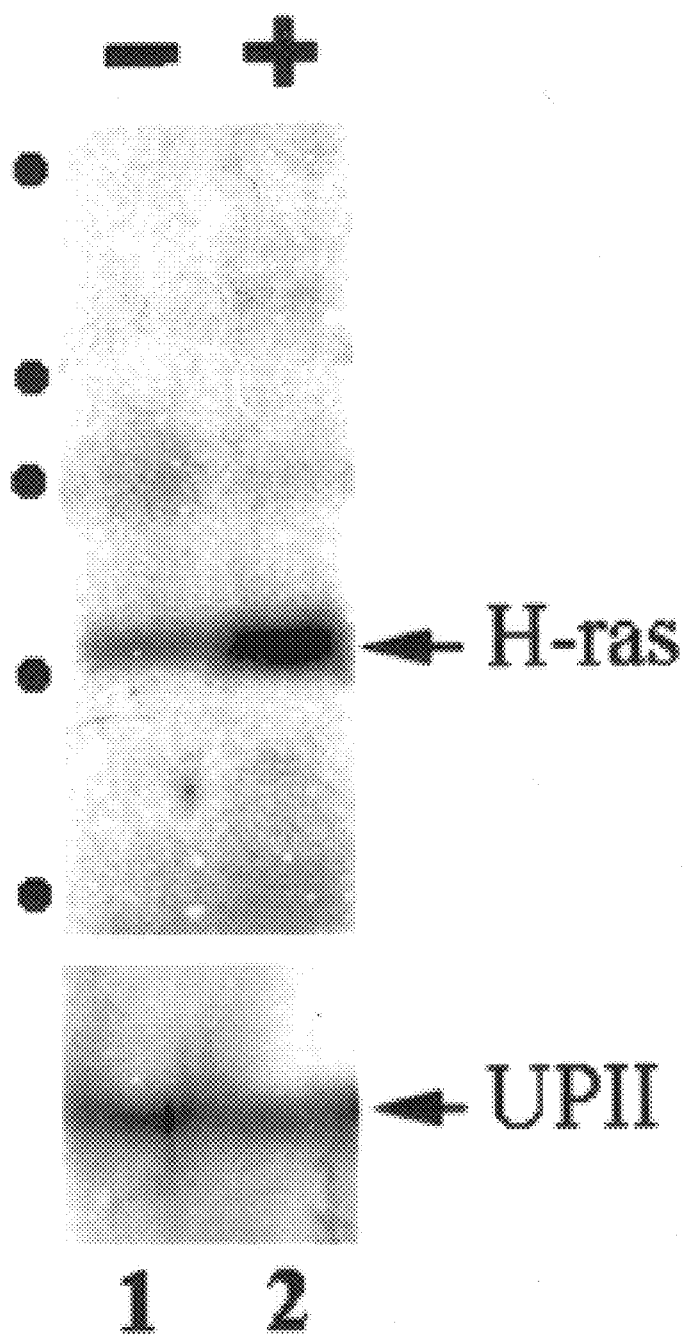
FIGS. 11A and 11B show immunoblotting of ras protein in mouse bladders. Total urothelial proteins from normal (−) and transgenic (+) mouse bladders were resolved by SDS-PAGE, and immunoblotted with a pan-ras antibody (FIG. 11A). Note the detection of a 21 kDa ras band that is more abundant in transgenic than in normal control bladders. The diffuse pattern of ras band in transgenic mice is due to the fast-migrating ras mutant (Corominas et al., 1991a).

Unlike SV40 Tag mice that developed aggressive bladder cancers, mice harboring a mutated c-H-ras had a more benign course of tumor development. Founder mouse ras-F0.2 that harbored 10 copies of transgenes developed a superficial bladder tumor at 3 months of age. The histological, immunohistochemical and immunofluorescent staining were performed generally as described in Example 3 above. Grossly, the tumor appeared as a peduculated, narrow-based polyp protruding into the bladder lumen. Histologically, the urothelium was markedly thickened with 10–20 layers of cells (FIG. 10A). However, the proliferating epithelial cells are very well-differentiated with abundant cytoplasm, and little nuclear atypia, pleomorphism or mitosis. Interestingly, within the proliferative tumor epithelium there were frequent slit-like appearances, much like the pseudoglandular formation that is relatively commonly observed in human TCCs (FIGS. 10A and 10B) (Eble et al, 1997). Also common were neovascularizations within the tumor epithelium (FIG. 10B). Immunohistochemical staining and immunoblotting using a pan-ras antibody revealed a high level of ras expression in tumor cells as compared with normal urothelium (FIGS. 10C, 10D and FIGS. 11A and 11B). Although founder mice F0.5 and F0.12 that harbor lower copy number of transgenes have not yet developed bladder tumors up to 7 months of age, their urothelium exhibited marked hyperproliferative changes with the loss of epithelial polarity and characteristic umbrella cells (FIG. 10E). Collectively, these results suggest that the activating mutation of H-ras proto-oncogene can be a relatively early event in initiating bladder tumorigenesis and support the earlier observation by Cohen and colleagues that overexpression of activated ras alone can be sufficient for malignant transformation (Mann et al, 1991). The fact that this activated H-ras induced a superficial, well-differentiated bladder tumor, but not the CIS or the invasive phenotype, is intriguing as it suggests that different genetic events may indeed underlie the pathogenesis of two different forms of bladder cancer.

EXAMPLE 5

Generation of Two Transgenic Mouse Lines Expressing a Dominant-Negative p53 Mutant The mutation and/or deletion of p53 tumor suppressor gene is the most common genetic alteration identified in human bladder cancer (Vogelstein et al, 1993). Knockout mice with germline deletion of both alleles of p53 gene are compatible with normal development, but are particularly susceptible to tumor formation, such as sarcoma and lymphoma, and succumb to death relatively early in life (Donehower et al, 1992). These mice are, therefore, not suitable for studying bladder cancer formation. An alternative approach is to inactivate p53 specifically in the bladder using dominant-negative p53 mutants. One such mutant is the N-terminal deletion mutant in which the DNA binding domain of p53 has been deleted, leaving the oligomerization C-terminal domain intact (Shaulian et al, 1992). When introduced into target cells, this mutant forms a stable complex with wild-type p53, thus functionally inactivating endogenous p53. Previous studies showed that this mutant could transform cells in culture. Recently, Bowman et al (1996) demonstrated in a brain tumor model that the tissue-specific expression of this p53 mutant in vivo dominantly inactivated wild-type p53 function and accelerated tumor progression.

Figure 12:
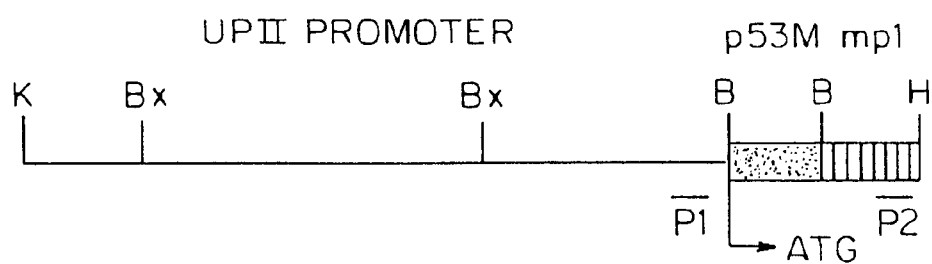
FIG. 12 schematically shows the transgene construct containing a 3.6 kb murine UPII promoter, a 0.3 kb p53 cDNA mutant and 0.5 kb mouse protamine 1 (mp1) polyadenylation sequence. P1 and P2 denote a mouse UPII probe and an mp1 probe designed to detect transgenes in transgenic mice in FIG. 13.

Construction of Transgene: Two transgenic mouse lines expressing the dominant-negative p53 mutant were generated in the laboratory of the present inventors, the UPII-p53M transgene was constructed by fusing the murine uroplakin II gene promoter with a deletion mutant of mouse p53 cDNA fragment, using the pUPII-LacZ as a host vector (Lin et al, 1995). Briefly, the p53 deletion mutant (containing sequences encoding the first 14 and last 89 amino acids of p53) was generated by PCR amplification of a PCMVDD p53 deletion vector (Arai et al, 1986). The oligonucleotide primers used were SEQ ID NO:7 (sense) and SEQ ID NO:8. A BamHI site was added to the ends of both sense and antisense primers to facilitate the sub-cloning. The PCR product was sub-cloned into a TA cloning vector and then digested with BamHI. For the construction of the transgene, pUPII-Lac plasmid was restriction-digested with BamHI to delete the LacZ sequence. The BamHI PCR fragment containing the p53 mutant was inserted onto the BamHI site of the BamHI-digested pUPII-LacZ. In the transgene tandem are the murine uroplakin II promoter, the p53 deletion mutant and a mouse protamine 1 intron, the latter of which provides a polyadenylation signal (FIG. 12). The orientation of UPII promoter and p53 mutant was confirmed by PCR, DNA sequencing and restriction digestion.

Southern Blotting of Mouse Tail Genomic DNA: Transgene incorporation in founder animals was determined by Southern blot analysis. Briefly, mouse tail DNA was digested with BstXI and probed with a $^{32}$P-labeled, BamHI-HindIII(500 bp) mouse protamine 1 fragment. For the estimation of transgene copy number, a 600 bp BamHI-StuI fragment of UPII promoter was used as a probe to detect endogenous genes, as well as transgenes. The X-ray film of genomic Southern blot was subjected to densitometry for the calculation of the relative amount of transgenes.

Figure 13:
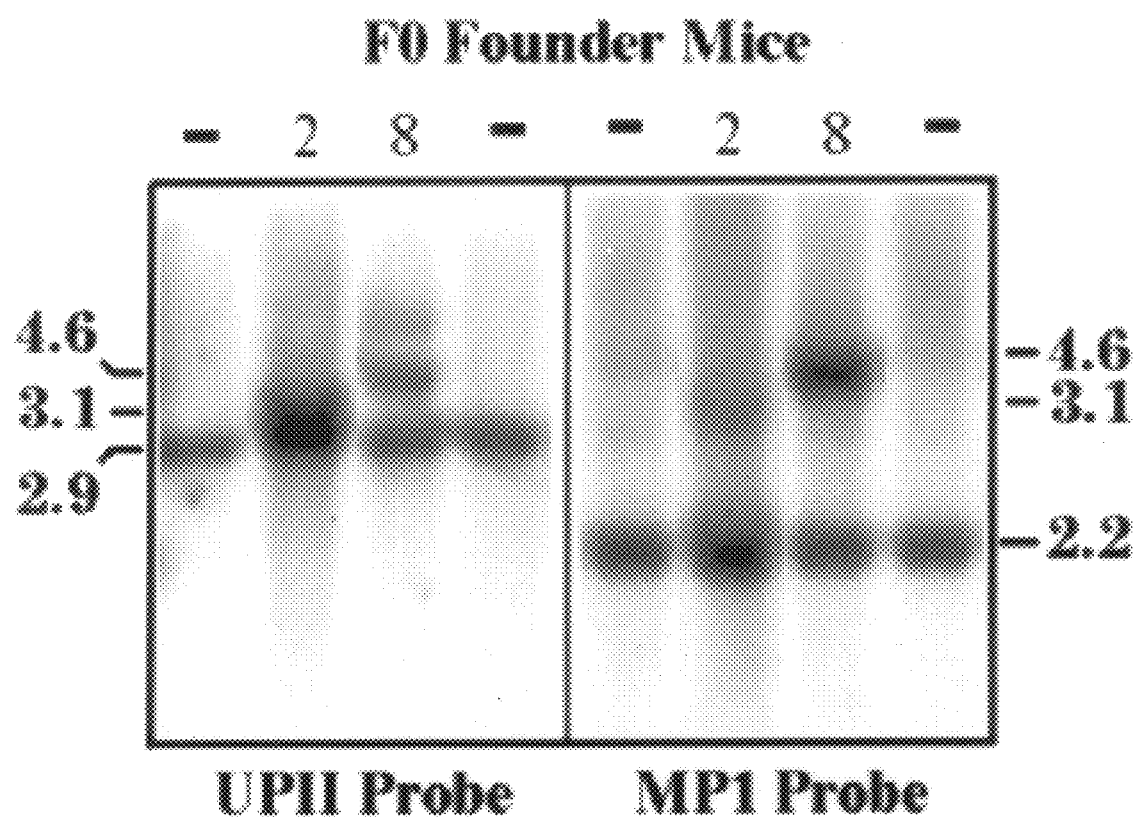
FIG. 13 shows Southern blot detection of mUPII/p53M transgenes. Mouse tail DNAs were digested by BstXI (Bx), electrophoresed, transferred onto nylon membrane and blotted with either a UPII probe or an mp1 probe. Note that two founder mice incorporated the transgene. The different sizes of restriction fragments of transgenes at 3.1 kb and 4.6 kb reflect a "head-to-tail" and "tail-to-tail" transgene orientation, respectively. (−) shows the transgene-negative control mice.
Figure 14:
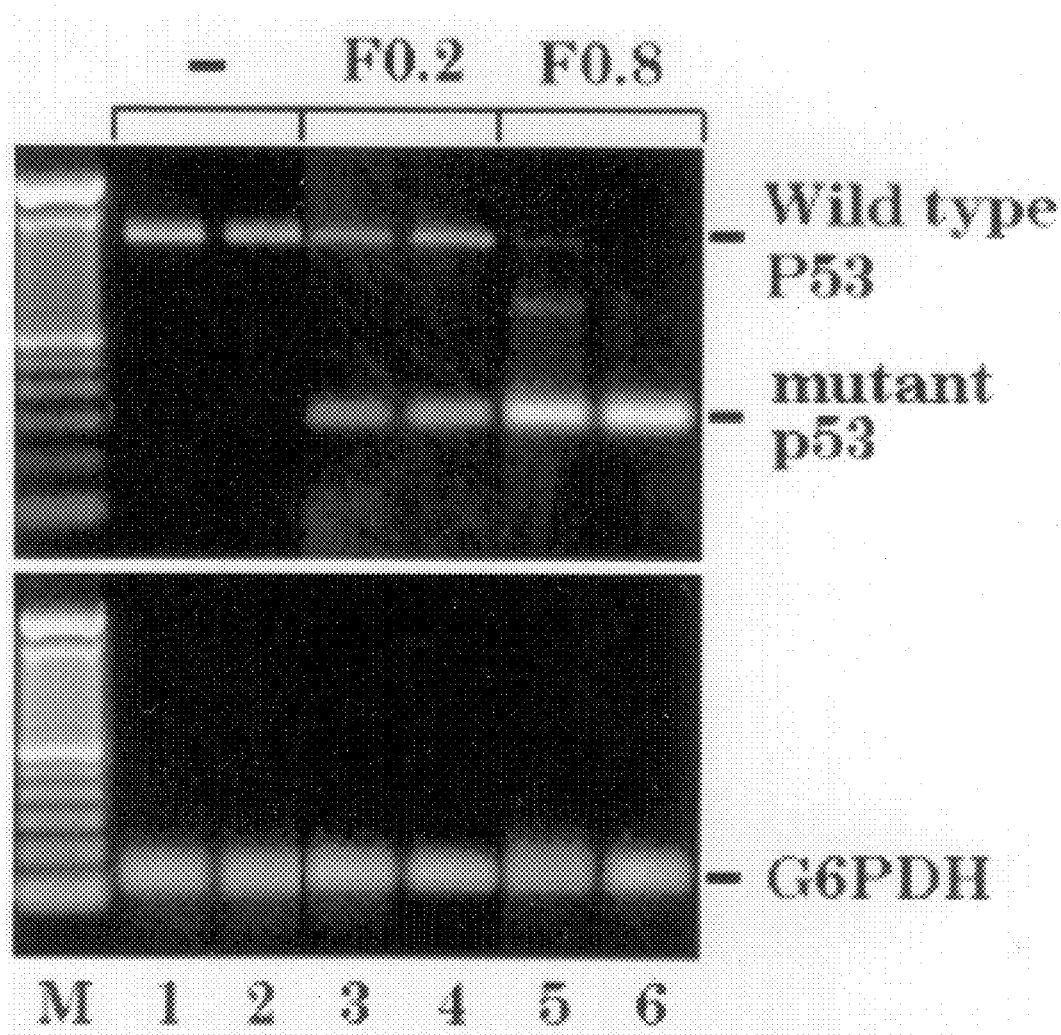
FIG. 14 shows RT-PCR analyses of p53 mutant expression in mouse bladders. Total RNAs were extracted from urothelial cells of transgenic F1 mice harboring mUPII/p53M transgene, and subjected to RT-PCR assay using two p53-specific primers. Note the detection of a 300 bp p53 mutant in transgenic lines, but not in negative controls (−). Also note the detection of a 1 kb endogenous wild type p53 product in all mice. Lower panel shows the product of a house-keeping cDNA (glucose-6-phosphate dehydrogenase, G6PDH), for RT-PCR normalization.

By Southern blotting, the two founder mice carried approximately two to three copies of the transgene, and both transmitted the transgene to F1 mice (FIG. 13). RT-PCR revealed that bladder epithelia of the two lines expressed the mRNAs corresponding to both wild type and mutant p53 (FIG. 14).

Having now fully described this invention, it will be appreciated that by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adams et al, *Nature*, 318:533–538 (1985).
Adams et al, *Science*, 254:1161–1167 (1991).
Arai et al, *Mol. Cell. Biol.*, 6:3232–3239 (1986).
Asamoto et al, *Acta Pathol. Jpn*, 40:322–326 (1990).
Babinet et al, *Genome*, 31:938–949 (1989).
Benedict et al, *J. Cell. Biochem. Supp.*, 16I:69–71 (1992).
Bernards et al, *Proc. Natl. Acad. Sci. USA* 86:6474–6478 (1989).
Berns, A., *J. Cell. Biochem.*, 47:130–135 (1991).
Bishop, J. M., *Cell*, 64:235–248 (1991).
Borland et al, *Hematol. Oncol. Clin. North Am.*, 6:31–39 (1992).
Bos, J. L., *Cancer Res.*, 49:4682–4689 (1989).
Bowman et al, *Genes Dev.*, 10:826–835 (1996).

Brinster et al, *Cell,* 27:223 (1981).
Bryan et al, *Crit. Rev. Oncog.,* 5:331–357 (1994).
Capon et al, *Nature,* 302:33–37 (1983).
Chaka et al, *Nature,* 314:377 (1985).
Chaka et al, *Nature,* 319:685 (1986).
Cohen, S. M., *Toxicology,* 102:149–159 (1995).
Coombs et al, *Br. J. Cancer,* 63:601–608 (1991).
Coopersmith et al, *J. Cell Biol.,* 138:167–179 (1997).
Cordon-Cardo et al, *Semin. Surg. Oncol.,* 13:319–327 (1997).
Cordon-Cardo et al, in *Important Advances in Oncology,* DeVita et al Eds., J. B. Lippincott Company, Philadelphia (1994).
Cordon-Cardo et al, *J. Natl. Cancer Inst.,* 84:1251–1256 (1992).
Corey et al, *Ann. Rev. Immunol.,* 6:25–48 (1988).
Corominas et al, *Environ. Health Perspect.,* 93:19–25 (1991a).
Corominas et al, *Oncogene,* 6(4):645–651 (1991b).
Costantini et al, *Nature,* 294:92 (1981).
Czerniak et al, *Hum. Pathol.,* 23:1199–1204 (1992).
Daya-Grosjean et al, *Cancer Res.,* 53:1625–1629 (1993).
Diatchenko et al, *Proc. Natl. Acad. Sci. USA,* 93:6025–6030 (1996).
Donehower et al, *Nature,* 356:215–221 (1992).
Eble et al, *Semin. Diagn. Pathol.,* 14:98–108 (1997).
Fearon et al, *Cell,* 61:759–767 (1990).
Fiers et al, *Nature,* 273:113–120 (1978).
Finlay, G. J., *Mutat. Res.,* 290:3–12 (1993).
Fowlis et al, *Eur. J. Cancer,* 29A:638–645 (1993).
Frohman et al, *Proc. Natl. Acad. Sci. USA,* 85:8998–9002 (1988).
Fujita et al, *Proc. Natl. Acad. Sci. USA,* 82:3849–3853 (1985).
Gordon et al, *Proc. Natl. Acad. Sci. USA,* 73:1260 (1976).
Grimm et al, *Urol. Res.,* 23:293–300 (1995).
Gruis et al, *Am. J. Pathol.,* 146:1199–1206 (1995).
Hammer et al, *Nature,* 315:680 (1985).
Hammer et al, *J. Animal Sci.,* 63:269 (1986).
Hammer et al, *Science,* 235:53 (1987).
Hanahan, D., *Nature,* 315:115–122 (1985).
Hanahan, D., *Science,* 246:1265–1275 (1989).
Harbers et al, *Nature,* 315:680 (1981).
Hicks, R. M., *J. Cell Biol.,* 26:25–48 (1965).
Hicks, R. M., *Biol. Rev.,* 50:215–246 (1975).
Hogan et al, *Manipulating the Mouse Embryo: A Laboratory Manual,* Cold Spring Harbor Laboratory (1986).
Hoskins et al, *Curr. Opin. Oncol.,* 6:554–559 (1994).
Hunter, T., *Cell,* 88:333–346 (1997).
Hynes et al, *Biochim. Biophys. Acta. Rev. Cancer,* 119:165–184 (1994).
Jaenisch, R., *Science,* 240:1468–1474 (1988).
Kamb et al, *Science,* 264:436–440 (1994).
Knowles et al, *Lab. Invest.,* 21:154–168 (1995).
Kollias et al, *Cell,* 46:89 (1986).
Koss, L. G., *Lab. Invest.,* 21:154–168 (1969).
Koss, L. G., in *Atlas of Tumor Pathology,* 2nd. series, Fasc. II, Suppl. Washington D.C.: Armed Forces Institute of Pathology (1985).
Koss, L. G., *J. Cell. Biochem. Supp.,* 16I:23–29 (1992).
Kotake et al, *Jpn. J. Cancer Res.,* 81:1198–1201 (1990).
Kubota et al, *J. Urol.,* 154:371–374 (1995).
Lacey et al, *Nature,* 322:609–612 (1986).
Landel et al, *Ann. Rev. Physiol.,* 52:841–851 (1990).
Levesque et al, *Int. J. Cancer,* 55:785–790 (1993).
Levine, A. J., *Cell,* 88:323–331 (1997).
Li et al, *Am. J. Pathol.,* 144:303–309 (1994).
Lin et al, *J. Biol. Chem.,* 269:1775–1784 (1994).
Lin et al, *Proc. Natl. Acad. Sci. USA,* 92:679–683 (1995).
Lipponen, P. K., *J. Pathol.,* 175:203–210 (1995).
Mann et al, *Oncogene Res.,* 6:65–72 (1991).
Masters et al, *Urol. Res.,* 16:341–344 (1988).
Mercer et al, *Neuron,* 7:703–716 (1991).
Moll, et al, *Am. J. Pathol.,* 157:1383–1397 (1995).
Orlow et al, *J. Natl. Cancer Inst.,* 86:1524–1529 (1995).
Palmiter et al, *Science,* 222:809 (1983).
Palmiter et al, *Ann. Rev. Genet.,* 20:465–499 (1986).
Paulovich et al, *Cell,* 88:315–321 (1997).
Peschan et al, *Proc. Natl. Acad. Sci. USA,* 84:5316–5319 (1987).
Porter et al, *An Introduction to the Fine Structure of Cells and Tissues,* Lea and Febiger, New York (1963).
Pulciani et al, *Proc. Natl. Acad. Sci. USA,* 79:2845–2849 (1987).
Ratlif et al, *Cancer Res.,* 44:4377–4381 (1984).
Ratlif, T. L., *Eur. Urol.,* 21(supp):17–21 (1992).
Reznikoff et al, *Semin. Oncol.,* 23:571–584 (1996).
Ryan et al, *Mamm. Genome,* 4:65a6–661 (1993).
Sauter et al, *Am. J. Pathol.,* 146:1131–1139 (1995).
Schmitz-Drager et al, *Urol. Res.,* 25(supp):S45–S49 (1997).
Serrano et al, *Cell,* 85:27–37 (1996).
Serrano et al, *Cell,* 88:593–602 (1997).
Shani, M., *Mol. Cell. Biol.,* 6:2624 (1986).
Shaulian et al, *Mol. Cell Biol.,* 12:5581–5592 (1992).
Silverberg et al, *CA-Cancer. J. Clin.,* 40:9–26 (1990).
Simon et al, *Bio/Technology,* 6:179–183 (1988).
Staehelin, L. A., *J. Cell Biol.,* 53:73–91 (1972).
Stanton et al, *Nature,* 310:423–425 (1984).
Stewart et al, *Science,* 217:1046–1048 (1982).
Stewart et al, *Cell,* 38:627–637 (1984).
Tennant et al, *Environ. Health Perspect.,* 103:942–950 (1995).
Townes et al, *EMBO J.,* 4:1715 (1985).
Vogelstein et al, *Cell,* 70:523–526 (1992).
Vogelstein et al, *Trends Genet.,* 9:138–141 (1993).
Wagner et al, *Proc. Natl. Acad. Sci. USA,* 78:5016 (1981).
Wagner et al, *Theriogenology,* 21:29 (1984).
Weinberg, R. A., *Science,* 254:1138–1146 (1991).
Witkowski, J. A. *Cancer Cells,* 229–257 (1990).
Wu et al, *J. Biol. Chem.* 265:19170–19179 (1990).
Wu et al, *J. Cell Sci.,* 106:31–43 (1993).
Wu et al, *J. Biol. Chem.* 269–13716–13724 (1994).
Wu et al, *Cancer Res.,* 58:1291–1297 (1998).
Yamamoto et al, *Nature,* 319:230–234 (1986).
Yu et al, *J. Cell Biol.,* 111:1207–1216 (1990).
Yu et al, *Epithelial Cell Biol.,* 1:4–12 (1992).
Yu et al, *J. Cell Biol.* 125:171–182 (1994).
Zakut-Houri et al, *Nature,* 306:594–597 (1983).
Zhang et al, *Proc. Natl. Acad. Sci. USA,* 95:2429–2434 (1998).
Zhau et al, *Mol. Carcinogen.,* 3:254–257 (1990).

What is claimed is:

1. A transgenic mouse all of whose germ cells and somatic cells contain one or more recombinant constructs of an oncogene or a functionally inactivated tumor suppressor gene, each of said oncogene or functionally inactivated tumor suppressor gene being operably linked to a uroplakin promoter and said one or more recombinant constructs having been introduced into said mouse, or an ancestor of said mouse, at an embryonic stage, wherein said mouse exhibits the phenotype for progression or development of tumors in the bladder and wherein said transgene is expressed in the urothelium at a level sufficient to result in tumor growth in the bladder.

2. The transgenic mouse according to claim 1, wherein said uroplakin promoter is uroplakin II promoter.

3. The transgenic mouse according to claim 2, wherein said uroplakin II promoter is mouse uroplakin II promoter.

4. The transgenic mouse according to claim 3, wherein said oncogene operably linked to said mouse uroplakin II promoter is SV40 large T antigen.

5. The transgenic mouse according to claim 3, wherein said oncogene operably linked to said mouse uroplakin II promoter is H-ras.

6. The transgenic mouse according to claim 3, wherein said functionally inactivated tumor suppressor gene operably linked to said mouse uroplakin II promoter is p53.

7. The transgenic mouse according to claim 1, wherein said oncogene is selected from the group consisting of SV40 large T antigen, H-ras, Neu/erbB-2, and c-myc.

8. The transgenic mouse according to claim 1, wherein said functionally inactivated tumor suppressor gene is selected from the group consisting of functionally inactivated p53, p16, and retinoblastoma gene.

9. The transgenic mouse according to claim 1, wherein said uroplakin promoter is selected from the group consisting of uroplakin Ia, uroplakin Ib, uroplakin II and uroplakin III.

\* \* \* \* \*